US009327038B2

(12) United States Patent
Di Pasqua et al.

(10) Patent No.: US 9,327,038 B2
(45) Date of Patent: May 3, 2016

(54) STABLE ACTIVATABLE PARTICLES AS RADIOTHERAPEUTIC AGENTS FOR THE TREATMENT OF DISEASE

(71) Applicant: The University of North Carolina at Chapel Hill, Chapel Hill, NC (US)

(72) Inventors: Anthony J. Di Pasqua, Fort Worth, TX (US); Xiuling Lu, Willington, CT (US); Michael Jay, Chapel Hill, NC (US)

(73) Assignee: The University of North Carolina at Chapel Hill, Chapel Hill, NC (US)

(*) Notice: Subject to any disclaimer, the term of this patent is extended or adjusted under 35 U.S.C. 154(b) by 550 days.

(21) Appl. No.: 13/660,198

(22) Filed: Oct. 25, 2012

(65) Prior Publication Data

US 2013/0101505 A1 Apr. 25, 2013

Related U.S. Application Data

(60) Provisional application No. 61/551,108, filed on Oct. 25, 2011.

(51) Int. Cl.
*A61K 51/00* (2006.01)
*A61M 36/14* (2006.01)
*A61K 51/12* (2006.01)

(52) U.S. Cl.
CPC ......... *A61K 51/1244* (2013.01); *A61K 51/1227* (2013.01)

(58) Field of Classification Search
CPC ........... A61K 2123/00; A61K 2121/00; A61K 51/00; A61K 51/02; A61K 51/1227; A61K 51/124422; B82Y 30/00; B82Y 5/00; C01P 2004/00; C01P 2004/51; C01P 2004/60; C01P 2004/61; C01P 2004/62; C01P 2004/64
USPC ............... 424/1.11, 1.61, 1.81, 9.1, 400, 489, 424/490, 1.29, 1.65; 514/1, 19.2; 977/773
See application file for complete search history.

(56) References Cited

U.S. PATENT DOCUMENTS

| 6,455,024 | B1* | 9/2002 | Glajch et al. | 424/1.33 |
| 7,959,900 | B2* | 6/2011 | Peng et al. | 424/1.11 |
| 2004/0022840 | A1 | 2/2004 | Nagy et al. | |
| 2007/0237826 | A1 | 10/2007 | Rao | |

OTHER PUBLICATIONS

Mumper et al, Pharmaceutical Research, 1992, vol. 9, No. 1, pp. 149-154.*
Hamoudeh et al (Drug Development and Industrial Pharmacy, 2008, vol. 34, pp. 796-806).*
Mumper et al (Pharmaceutical Research, 1992, vol. 9, No1. 1, pp. 149-154).*
Cabellos (Thesis: Synthesis of gamma-Fe2O3-SiO2 composite nanoparticles targeting magnetic resonance imaging and magnetitic hyperthermia applications, 233 pages total).*
Advancing Nuclear Medicine Through Innovation, Committee on State of the Science of Nuclear Medicine, National Research Council, *Targeted Nucleotide Therapy*, 4.1, 2007, The National Academies Press, Washington D.C, 174 pages.
Aetna, Inc. Clinical Policy Bulletin: Radioimmunotherapy for Non-Hodgkin's Lymphoma: Ibritumomab Tiuxetan (Zevalin) and Tositumomab (Bexxar), 2011, 10 pages.
Aliabadi et al., "Polymeric micelles for drug delivery", *Expert Opin. Drug Deliv.*, Jan. 2006, vol. 3, No. 1, pp. 139-162.
Bult W. et al., "Holmium Nanoparticles: Preparation and in Vitro Characterization of a New Device for Radioablation of Solid Malignancies", *Pharm Res.*, 2010, 27:2205-2212.
Croy S.R. et al., "Polymeric micelles for drug delivery", *Curr Pharm Des.*, 2006; 12(36):4669-84.
Di Pasqua A.J. et al., "Neutron-Activatable Holmium-Containing Mesoporous Silica Nanoparticles as a Potential Radionuclide Therapeutic Agent for Ovarian Cancer", *J. Nucl. Med.*, 2013; 54:111-116.
Di Pasqua A.J. et al., "Preparation of Neutron-Activatable Holmium Nanoparticles for the Treatment of Ovarian Cancer Metastases", *Small*, 2012, 8, No. 7, 997-1000.
Di Pasqua A.J. et al., "Tumor accumulation of neutron-activatable holmium-containing mesoporous silica nanoparticles in an orthotopic non-small cell lung cancer mouse model", *Inorganica Chimica Acta*, vol. 393, Dec. 2012, pp. 334-336.
Grifman M. et al., "Incorporation of Tumor-Targeting Peptides into Recombinant Adeno-associated Virus Capsids", *Molecular Therapy*, vol. 3, No. 6, Jun. 2001, 964-975.
Kim et al., "Preparation and Characterization of Stearic Acid-Pullulan Nanoparticles", *Arch Pharm Res*, vol. 33, No. 5, 761-767, 2010.
Konda S.D. et al., "Development of a Tumor-Targeting MR Contrast Agent Using the High-Affinity Folate Receptor: Work in Progress", *Investigative Radiology*, Jan. 2000, vol. 35, Issue 1, p. 50.
Kreuter J., "Nanoparticles and microparticles for drug and vaccine delivery", *J. Anat.*, 1996, 189, pp. 503-505.
Kwon G.S., "Polymeric micelles for delivery of poorly water-soluble compounds", *Crit Rev Ther Drug Carrier Syst*, 2003;20(5):357-403 (Abstract Only).
Kwon S. et al., "Synthesis of biocompatible and biodegradable polymer particles in supercritical carbon dioxide", *Colloid Polym Sci*, 2008, 286:1181-1191.
Mumper R. et al., "Neutron-Activated Holmium-166-Poly (L-Lactic Acid) Microspheres: A Potential Agent for the Internal Radiation Therapy of Hepatic Tumors", *J. Nucl. Med.*, 1991; 32:2139-2143.
Mumper R. et al., "Polymeric Microspheres for Radionuclide Synovectomy Containing Neutron-Activated Holmium-166", *J. Nucl. Med.*, 1992; 33:398-402.
Nijsen J.F.W. et al., "Holmium-166 poly lactic acid microspheres applicable for intra-arterial radionuclide therapy of hepatic malignancies: effects of preparation and neutron activation techniques", *Eur. J. Nucl. Med.*, 1999, 26:699-704.
Ojima I., "Guided Molecular Missiles for Tumor-Targeting Chemotherapy-Case Studies Using the Second-Generation Taxoids as Warheads", *Accounts of Chemical Research*, 108-119, Jan. 2008, vol. 41, No. 1.
Qian X. et al., "In vivo tumor targeting and spectroscopic detection with surface-enhanced Raman nanoparticle tags", *Nature Biotechnology*, vol. 26, No. 1, Jan. 2008, 83-90.
Rowe R.C. et al., Handbook of Pharmaceutical Excipients, 6th Edition, Published by The Pharmaceutical Press and American Pharmacists Association, 2009, 917 pages.
Spencer T. et al., "Intraperitoneal P-32 After Negative Second-Look Laparotomy in Ovarian Carcinoma", *Cancer*, 63:2434-2437, 1989.

* cited by examiner

*Primary Examiner* — D L Jones
(74) *Attorney, Agent, or Firm* — Myers Bigel & Sibley, P.A.

(57) ABSTRACT

The present invention provides radiotherapeutic agents and compositions and methods for making and using the same. In some embodiments, the radiotherapeutic agent is a nanoparticle comprising a radionuclide and a carrier moiety. In some embodiments, the radionuclide is produced by activating a stable activatable particle via neutron activation.

11 Claims, 17 Drawing Sheets

STABLE ACTIVATABLE PARTICLES AS RADIOTHERAPEUTIC AGENTS FOR THE TREATMENT OF DISEASE

RELATED APPLICATION

This application claims priority under 35 U.S.C. §119(e) to U.S. Provisional Patent Application No. 61/551,108, filed Oct. 25, 2011, the disclosure of which is incorporated herein by reference in its entirety.

FIELD OF THE INVENTION

The present invention relates to radiotherapeutic agents and the treatment of disorders responsive to radiotherapeutic agents.

BACKGROUND

Administration of therapeutic radionuclides that are targeted to specific tumor cells has been used against a variety of tumors. Targeted radionuclide therapy in which radionuclides contained within particle-based carrier moiety systems emit ionizing radiation that is absorbed by target cancer cells has significant potential for personalized cancer therapies. The targeting agent and the absorbed radiation dose delivered by radionuclide-containing particles can be tailored to the individual patient. If the tumor uptake of the radionuclide-containing particles can also be assessed through high-resolution imaging, then treatment planning and dosimetric modeling can be used to determine the best combination of radionuclide and targeting agent for treating the tumor while sparing non-cancerous tissues. This can be followed by adaptive radiotherapy in which molecular imaging with specific targeting agents may allow clinicians to evaluate the response to radionuclide therapy and adjust subsequent treatments to the altered status of the tumor cells resulting from changes in the receptor target populations on tumor cells. The flexibility of this approach makes particle-based targeted radionuclide therapy an attractive approach for cancer treatment.

According to the National Academies Collection, reports on Targeted Radionuclide Therapy that are funded by NIH reveal that there are currently four targeted radiotherapeutics approved by the FDA for human use, all of which employ beta-emitting radionuclides. Committee on State of the Science of Nuclear Medicine, National Research Council, *Targeted Nucleotide Therapy*, in ADVANCING NUCLEAR MEDICINE THROUGH INNOVATION, at 4.1 (National Academies Press) (2007). These include monoclonal antibodies labeled with $^{90}$Y (Zevalin®; Spectrum Pharmaceuticals, Inc., Hendersen, Nev.) or $^{131}$I (Bexxar®; GlaxoSmithKline, Philadelphia, Pa.) for the treatment of B-cell lymphoma and related cancers. Excellent clinical results have been observed with these agents (overall response rate of 60-80% and complete response rates of 20-40% for patients with relapsed, recurrent, or refractory indolent B-cell lymphoma). AETNA, INC., CLINICAL POLICY BULLETIN: RADIOIMMUNOTHERAPY FOR NON-HODGKIN'S LYMPHOMA: IBRITUMOMAB TIUXETAN (ZEVALIN) AND TOSITUMOMAB (BEXXAR) (2011). This is similar to the response rate obtained with multiple cycles of conventional chemotherapy, but with a much lower incidence of toxicity. The other FDA-approved radiotherapeutics are $^{153}$Sm-EDTMP (Quadramet®; EUSA Pharma (USA), Inc., Langhorne, Pa.) and $^{89}$Sr chloride (Metastron®; GE Healthcare, Buckinghamshire, UK) for palliation of bone metastases. In addition, a non-targeted radiotherapeutic agent, Chromic [$^{32}$P] phosphate (Phosphocol®; Mallinckrodt, St. Louis, Mo.) has been administered via intraperitoneal (i.p.) injection as a palliative treatment of ovarian cancer. Spencer et al., *Intraperitoneal P-32 after negative second-look laparotomy in ovarian carcinoma*, CANCER 63:2434 (1989). There are a number of other radiotherapeutic agents in the preclinical and clinical stages of research that use beta-emitter radionuclides such as holmium-166 (166Ho).

$^{166}$Ho is an attractive candidate for use as a therapeutic radionuclide because of its relatively short half-life (26.8 h), which allows for greater control of dosage, time of exposure, etc., and because it emits both high energy beta particles and gamma rays (6.6% photon yield), which allows it to be used for both radioablation and nuclear imaging (e.g., its distribution may to be quantified and imaged after administration). Furthermore, $^{166}$Ho's high attenuation coefficient and paramagnetic properties allow it be visualized using x-ray computed tomography (CT) and magnetic resonance imaging (MRI).

The present invention addresses concerns regarding the handling of large amounts of radioactivity during the preparation, storage and transport of therapeutic radionuclides by providing a stable activatable particle that may be produced in a non-radioactive state and subsequently activated to produce a radiotherapeutic agent. Because the stable activatable particles are manufactured in a non-radioactive state, careful quality control measures may be employed (to ensure proper particle size distribution, for example) and FDA manufacturing guidelines may be adhered to without the constraints imposed by the handling of radioactive materials.

SUMMARY OF THE INVENTION

The present invention provides radiotherapeutic agents and compositions and methods for making and using the same.

A first aspect of the present invention is a stable activatable particle comprising, consisting essentially of or consisting of an activatable radionuclide precursor and a carrier moiety.

A further aspect of the present invention is a radiotherapeutic agent comprising, consisting essential of or consisting of a radionuclide and a carrier moiety.

A further aspect of the present invention is a pharmaceutical composition comprising, consisting essentially of or consisting of a radiotherapeutic agent and a pharmaceutically acceptable carrier.

A further aspect of the present invention is a method of producing a stable activatable particle, comprising, consisting essentially of or consisting of conjugating a hydrophobic and/or lipophilic activatable radionuclide precursor to a carrier moiety.

A further aspect of the present invention is a method of producing a radiotherapeutic agent, comprising, consisting essentially of or consisting of activating a stable activatable particle of the present invention.

A further aspect of the present invention is a method of treating a disorder in a subject in need thereof, comprising, consisting essentially of or consisting of administering to said subject a therapeutically effective amount of a radiotherapeutic agent and/or pharmaceutical composition of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A is a photograph of a SKOV-3 ovarian tumor mouse with intraperitoneal metastasis 24 hours after intraperitoneal injection of $^{166}$Ho-MCM-41 nanoparticles (approximately 650 µCi). FIG. 2B is a SPECT/CT image of the same mouse one hour after the aforementioned injection.

FIG. 5A contains $^{18}$F-2-fluoro-2-deoxy-D-glucose ($^{18}$F-FDG) positron emission tomography/computed tomography (PET/CT) images of SKOV-3 ovarian tumor mice before (0 days) and 6, 13 and 20 days after injection with $^{165}$Ho-MCM-41 nanoparticles or $^{166}$Ho-MCM-41 nanoparticles. FIG. 5B is a graph showing $^{18}$F-FDG uptake in the two groups over time, wherein $^{18}$F-FDG uptake at each time point is shown relative to $^{18}$F-FDG uptake on day 0.

FIG. 11A is a coronal view SPEC/CT image of an SKOV-3 ovarian tumor mouse with intraperitoneal metastasis acquired one hour after intraperitoneal injection with folate-targeted $^{166}$Ho-DSPE nanoparticles. FIG. 11B is a sagittal view SPEC/CT image of an SKOV-3 ovarian tumor mouse with intraperitoneal metastasis acquired one hour after intraperitoneal injection with folate-targeted $^{166}$Ho-DSPE nanoparticles. FIG. 11C is a coronal view SPEC/CT image of an SKOV-3 ovarian tumor mouse with intraperitoneal metastasis acquired 24 hours after intraperitoneal injection with folate-targeted $^{166}$Ho-DSPE nanoparticles. FIG. 11D is a sagittal view SPEC/CT image of an SKOV-3 ovarian tumor mouse with intraperitoneal metastasis acquired 24 hours after intraperitoneal injection with folate-targeted $^{166}$Ho-DSPE nanoparticles. FIG. 11E is a MRI image of an SKOV-3 ovarian tumor mouse with intraperitoneal metastasis.

FIG. 15A is a bioluminescence image of NSCLC A549-luciferase tumor-bearing mice two weeks after implantation of NSCLC A549-luc-C8 cells. FIG. 15B shows the biodistribution of $^{166}$Ho-MCM-41 nanoparticles following intravenous injection in NSCLC A549-luciferase tumor-bearing mice. "$^{166}$Ho-MCM-41, 24 h" represents data acquired 24 hours after injection with $^{166}$Ho-MCM-41 nanoparticles (approximately 150 µCi). "$^{166}$Ho-MCM-41, 1 wk" represents data acquired one week after injection with $^{166}$Ho-MCM-41 nanoparticles (approximately 300 µCi). "$^{166}$Ho(AcAc)$_3$, 24 h" represents data acquired 24 hours after injection with $^{166}$Ho(AcAc)$_3$. "$^{166}$Ho(AcAc)$_3$, 1 wk" represents data acquired one week after injection with $^{166}$Ho(AcAc)$_3$.

DETAILED DESCRIPTION

Figure 1:
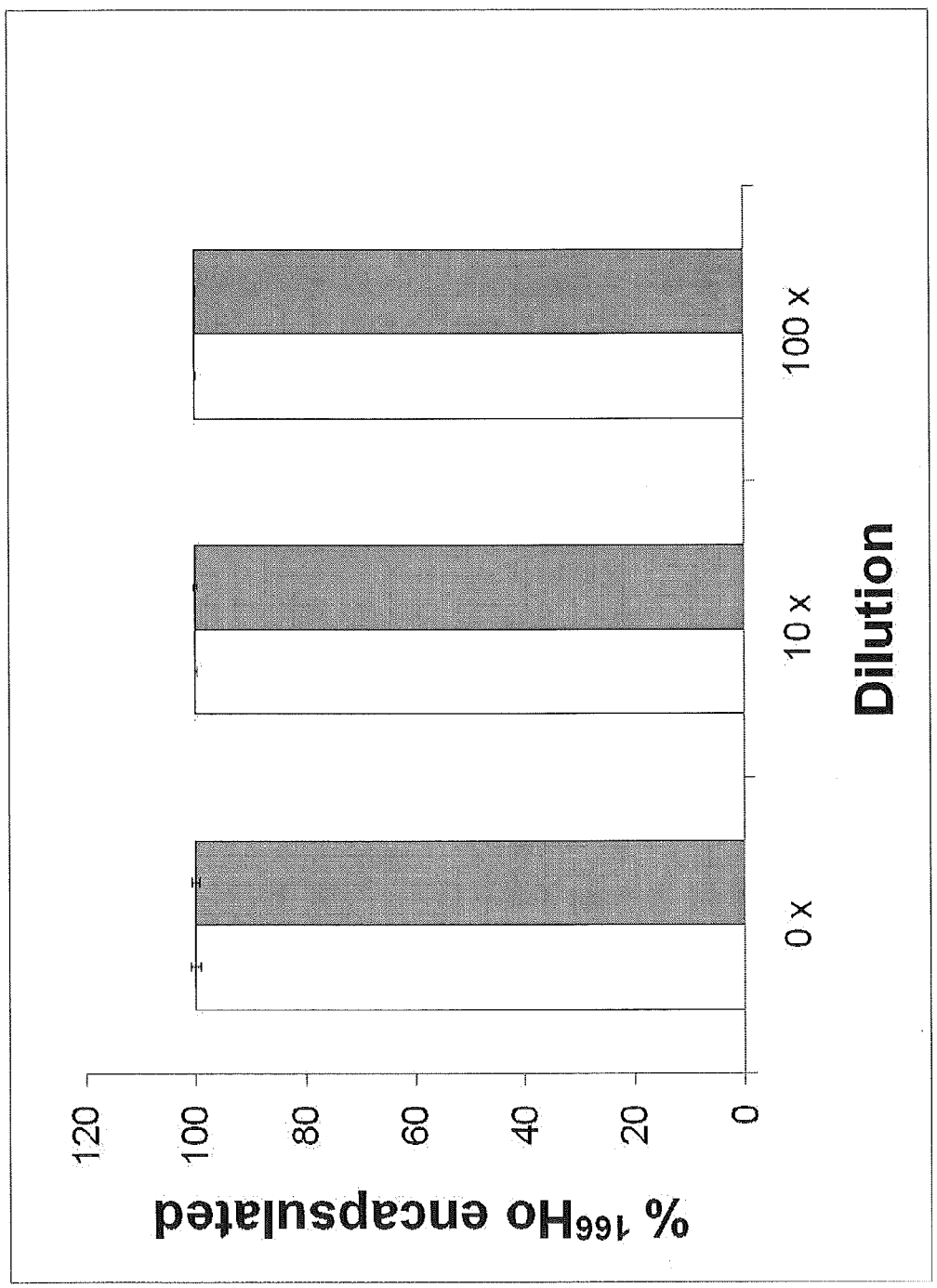
FIG. 1 shows that a radiotherapeutic agent of the present invention ($^{166}$Ho-MCM-41 nanoparticles) retained approximately 100% of its radionuclide ($^{166}$Ho) following dilution and extended incubation at 37° C. White bars represent data acquired immediately following neutron activation and dilution in phosphate buffered saline (PBS), pH 7.4. Gray bars represent data acquired after neutron activation, dilution in phosphate buffered saline (PBS), pH 7.4, and incubation at 37° C. for 24 hours.

The foregoing and other aspects of the present invention will now be described in more detail with respect to the description and methodologies provided herein. This description is not intended to be a detailed catalogue of all the ways in which the present invention may be implemented, or of all the features that may be added to the present invention. For example, features illustrated with respect to one embodiment may be incorporated into other embodiments, and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following specification is intended to illustrate some particular embodiments of the invention, and not to exhaustively specify all permutations, combinations and variations thereof.

All patents, patent publications, non-patent publications and sequences referenced herein are incorporated by reference in their entireties.

DEFINITIONS

Although the following terms are believed to be well understood by one of skill in the art, the following definitions are set forth to facilitate understanding of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

As used herein, the terms "a" or "an" or "the" may refer to one or more than one. For example, "a" marker can mean one marker or a plurality of markers.

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, the term "activatable radionuclide precursor" refers to non-radioactive molecule that may be activated to produce a radionuclide.

As used herein, the term "and/or" refers to and encompasses any and all possible combinations of one or more of the associated listed items, as well as the lack of combinations when interpreted in the alternative ("or").

As used herein, the term "cancer" refers to any benign or malignant abnormal growth of cells. Examples include, without limitation, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In some embodiments, the cancer is selected from the group of tumor-forming cancers.

As used herein, the term "consists essentially of" (and grammatical variants thereof), as applied to the compositions and methods of the present invention, means that the compositions/methods may contain additional components so long as the additional components do not materially alter the composition/method. The term "materially alter," as applied to a composition/method, refers to an increase or decrease in the effectiveness of the composition/method of at least about 20% or more. For example, a component added to a composition of the present invention would "materially alter" the composition if it increases or decreases the composition's ability to inhibit tumor growth by at least 20%.

As used herein, the term "emulsion" refers to a suspension or dispersion of one liquid within a second immiscible liquid. In some embodiments, the emulsion is an oil-in-water emulsion or a water-in-oil emulsion. In some embodiments, "emulsion" may refer to a material that is a solid or semi-solid at room temperature and is a liquid at body temperature (about 37° C.).

As used herein, the terms "increase" and "enhance" (and grammatical variants thereof) refer to an increase in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more.

As used herein, the terms "inhibit" and "reduce" (and grammatical variants thereof) refer to a decrease in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more.

As used herein, the term "liposome" refers to an aqueous or aqueous-buffered compartment enclosed by a lipid bilayer. In general, liposomes can be prepared by a thin film hydration technique followed by a few freeze-thaw cycles. Liposomal suspensions can also be prepared according to other methods known to those skilled in the art.

As used herein, the term "mesoporous" refers to a material having pores with a diameter in the range of from about 0.5 nm to about 1 μm. In some embodiments, mesoporous materials have pores with a diameter in the range of from about 2 nm to about 50 nm.

As used herein, the term "microparticle" refers to a particle that is about 1 μm to about 1 mm in diameter. In some embodiments, the microparticle has a diameter of from about 5 μm to about 100 μm. In some embodiments, the microparticle is about 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 975 or 999 μm in diameter.

As used herein, the term "nanoparticle" refers to a particle that is about 0.5 nm to about 1 μm in diameter. In some embodiments, the nanoparticle has a diameter of from about 5 nm to about 100 nm. In some embodiments, the nanoparticle is about 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 975 or 999 nm in diameter.

As used herein, "pharmaceutically acceptable" means that the material is suitable for administration to a subject and will allow desired treatment to be carried out without giving rise to unduly deleterious side effects. The severity of the disease and the necessity of the treatment are generally taken into account when determining whether any particular side effect is unduly deleterious.

As used herein, the term "polymeric micelle" refers to a micelle comprising one or more amphiphilic copolymers.

As used herein, the term "radiotherapeutic agent" refers to a molecule or compound that emits radiation.

As used herein the term "radionuclide" refers to an atom with an unstable nucleus, which undergoes radioactive decay and emits gamma rays and/or subatomic particles.

As used herein, the term "solid lipid particle" refers to a particle having a solid lipid core. For example, the core may comprise one or more triglycerides, diglycerides, monoglycerides, fatty acids, steroids and/or waxes.

As used herein the term "stable activatable particle" refers to a non-radioactive particle that may be activated to produce a radiotherapeutic agent. In some embodiments, the stable activatable particle is a microparticle or a nanoparticle. In some embodiments, the stable activatable particle has a diameter of from about 0.5 nm to about 5.0 mm. In some embodiments, the stable activatable particle has a diameter of from about 100 µm to about 500 µm. In some embodiments, the stable activatable particle has a diameter of from about 5 µm to about 100 µm. In some embodiments, the stable activatable particle has a diameter of from about 100 nm to about 500 nm. In some embodiments, the stable activatable particle has a diameter of from about 5 nm to about 100 nm. In some embodiments, the stable activatable particle has a diameter of about 400 nm.

As used herein, the term "subject" (and grammatical variants thereof) refers to mammals, avians, reptiles, amphibians, or fish. Mammalian subjects may include, but are not limited to, humans, non-human primates (e.g., monkeys, chimpanzees, baboons, etc.), dogs, cats, mice, hamsters, rats, horses, cows, pigs, rabbits, sheep and goats. Avian subjects may include, but are not limited to, chickens, turkeys, ducks, geese, quail and pheasant, and birds kept as pets (e.g., parakeets, parrots, macaws, cockatoos, and the like). In particular embodiments, the subject is from an endangered species. In particular embodiments, the subject is a laboratory animal. Human subjects may include neonates, infants, juveniles, adults, and geriatric subjects.

As used herein, the term "therapeutically effective" refers to provision of some improvement or benefit to the subject. Alternatively stated, a "therapeutically effective amount" is an amount that will provide some alleviation, mitigation, or decrease in at least one clinical symptom in the subject (e.g., in the case of cancer, reduced tumor size, decreased incidence of metastasis, etc.). Those skilled in the art will appreciate that the therapeutic effects need not be complete or curative, as long as some benefit is provided to the subject.

As used herein, the terms "treatment," "treat," and "treating" refer to reversing, alleviating, delaying the onset of, inhibiting the progress of or preventing a disease or disorder. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

Compositions

The present invention provides radiotherapeutic agents and compositions for making and using the same.

A first aspect of the present invention is a stable activatable particle comprising, consisting essentially of or consisting of an activatable radionuclide precursor and a carrier moiety.

A further aspect of the present invention is a radiotherapeutic agent comprising, consistently essential of or consisting of a radionuclide and a carrier moiety.

A further aspect of the present invention is a pharmaceutical composition comprising, consisting essentially of or consisting of a stable activatable particle and a pharmaceutically acceptable carrier.

A further aspect of the present invention is a pharmaceutical composition comprising, consisting essentially of or consisting of a radiotherapeutic agent and a pharmaceutically acceptable carrier.

Stable Activatable Particles

The present invention provides stable activatable particles that comprise, consist essentially of or consist of an activatable radionuclide precursor and a carrier moiety. In some embodiments, the stable activatable particle is a stable activatable microparticle or a stable activatable nanoparticle.

I. Activatable Radionuclide Precursors

Stable activatable particles of the present invention may comprise any suitable activatable radionuclide precursor known in the art. In some embodiments, the activatable radionuclide precursor comprises, consists essentially of or consists of $^{23}$Na, $^{31}$P, $^{56}$Fe, $^{74}$Se, $^{85}$Rb, $^{88}$Sr, $^{89}$Y, $^{127}$I, $^{139}$La, $^{141}$Pr, $^{152}$Sm, $^{164}$Dy, $^{165}$Ho, $^{168}$Er, $^{175}$Lu, $^{185}$Re, $^{187}$Re, $^{197}$Au and/or $^{203}$Tl. In some embodiments, the activatable radionuclide precursor comprises, consists essentially of or consists of a stable lanthanide isotope that may be converted into a radioactive lanthanide isotope (via neutron activation, for example). In some embodiments, the activatable radionuclide precursor comprises, consists essentially of or consists of $^{31}$P, $^{88}$Sr, $^{89}$Y, $^{127}$I, $^{139}$La, $^{141}$Pr, $^{149}$Sm, $^{150}$Sm, $^{152}$Sm, $^{164}$Dy, $^{165}$Ho, $^{168}$Er, $^{175}$Lu $^{185}$Re and/or $^{187}$Re. In some embodiments, the activatable radionuclide precursor comprises, consists essentially of or consists of $^{165}$Ho.

In some embodiments, the activatable radionuclide precursor comprises, consists essentially of or consists of a radionuclide conjugated to a hydrophobic and/or lipophilic moiety. The activatable radionuclide precursor may be conjugated to any suitable hydrophobic and/or lipophilic moiety known in the art, including, but not limited to, 2,4-pentanedione (acetylacetone), ethyl acetoacetate, 3-methyl-2,4-pentanedione, 3-ethyl-2,4-pentanedione, 2,4-hexanedione and diethyl malonate. Any suitable method of conjugation known in the art may be used, including, but not limited to the method described in Example 1 below. In some embodiments, the activatable radionuclide precursor comprises, consists essentially of or consists of holmium-165 acetylacetonate ($^{165}$Ho (AcAc)$_3$).

Any suitable method known in the art may be used to activate the activatable radionuclide precursor, including, but not limited to, neutron activation. See, e.g., Bult et al., PHARM. RES. 27:2205 (2010); Di Pasqua et al., *Neutron-activatable holmium-containing mesoporous silica nanoparticles as a potential radionuclide therapeutic agent for ovarian cancer*, J. NUCL. MED. in press (2012); Di Pasqua et al., *Tumor accumulation of neutron-activatable holmium-containing mesoporous silica nanoparticles in an orthotopic non-small cell lung cancer mouse model*, INORGANICA CHIMICA ACTA in press (2012); Di Pasqua et al., SMALL 8:997 (2012); Mumper et al., J. NUCL. MED. 32(11):2139 (1991); Mumper et al., J. NUCL. MED. 33(3):398 (1992).

Activatable radionuclide precursors of the present invention may be synthesized via any suitable method known in the art. See, e.g., Bult et al., PHARM. RES. 27:2205 (2010); Di Pasqua et al., *Neutron-activatable holmium-containing mesoporous silica nanoparticles as a potential radionuclide therapeutic agent for ovarian cancer*, J. NUCL. MED. in press (2012); Di Pasqua et al., *Tumor accumulation of neutron-activatable holmium-containing mesoporous silica nanoparticles in an orthotopic non-small cell lung cancer mouse model*, INORGANICA CHIMICA ACTA in press (2012); Di Pasqua et al., SMALL 8:997 (2012); Mumper et al., J. NUCL. MED. 32(11): 2139 (1991); Mumper et al., J. NUCL. MED. 33(3):398 (1992); Nijsen et al., EUR. J. NUCL. MED. 26:699 (1999).

II. Carrier Moieties

Stable activatable particles of the present invention may comprise any suitable carrier moiety known in the art. In some embodiments, the carrier moiety is a micelle (e.g., a polymeric micelle). See, e.g., Aliabadi & Lavasanifar, EXPERT OPIN. DRUG DELIV. 3(1):139 (2006); Croy & Kwon, CURR. PHARM. DES. 12(36):4669 (2006); Kwon, CRIT. REV. THER. DRUG CARRIER MOIETY SYST. 20(5):357 (2003). In some embodiments, the carrier moiety is selected from the group consisting of microporous/mesoporous/macroporous silica particles (including, but not limited to, MCM-41, MCM-48, SBA-15, TUD-1, FSM-16, HMM-1, HMM33, KSW-1, KSW-2 and MSU-1 type silica particles), metallic oxide particles, biocompatible polymer particles, solid lipid particles, polymer-coated nanoparticles, poly(methyl methacrylate) particles, poly(alkyl cyanoacrylate) particles, polyacrylate particles, PS particles, PGA particles, PLA particles, PLGA particles and stearic acid-conjugated pullulan (SAP) particles. See generally U.S. Patent Publication Nos. 2004/0022840 and 2007/0237826; Kim and Oh, ARCH. PHARM. RES. 33:761-767 (2010); Kreuter, J. ANAT. 189:503 (1996); Kwon et al. COLLOID POLYM. SCI. 286:1181 (2008). In some embodiments, the carrier moiety is selected from the group consisting of a polymeric micelle, a solid lipid particle and a mesoporous silica particle. In some embodiments, the carrier moiety is an MCM-41 type mesoporous silica particle or 1,2-distearyol-sn-glycero-3-phosphoethanolamine-N-[methoxy(polyethylene glycol)] (DSPE-PEG). In some embodiments, the carrier moiety is a microparticle or a nanoparticle.

Carrier moieties of the present invention may be synthesized via any suitable method known in the art. See, e.g., U.S. Patent Publication Nos. 2004/0022840 and 2007/0237826; Di Pasqua et al., *Tumor accumulation of neutron-activatable holmium-containing mesoporous silica nanoparticles in an orthotopic non-small cell lung cancer mouse model*, INORGANICA CHIMICA ACTA in press (2012); Kreuter, J. ANAT. 189: 503 (1996). In some embodiments, the carrier moiety is an MCM-41 type mesoporous silica particle synthesized as follows:
1. heat a solution comprising 7 mL 2.0 M NaOH and 480 mL $H_2O$ to 80° C.;
2. 2.0 g of cetyltrimethylammonium bromide and 11.3 mL of tetraethyl orthosilicate are added to the solution of step 1, optionally while stirring the solution of step 1, thereby forming a white precipitate;
3. the white precipitate of step 2 is washed with $H_2O$ and absolute ethanol prior to being dried in vacuo;
4. 1.0 g of the washed, dried precipitate of step 3 is added to 150 mL absolute ethanol to form a wet precipitate;
5. 0.5 mL of concentrated HCl is added to the wet precipitate of step 4, optionally while stirring the wet precipitate of step 4;
6. the mixture of step 5 is incubated at 50° C. for 5 hours, thereby forming a calcined solid; and
7. the calcined solid of step 6 is washed with $H_2O$ and absolute ethanol prior to being dried in vacuo.

In some such embodiments, the MCM-41 type mesoporous silica particles have a diameter of between about 50 nm and about 500 nm (e.g., about 400 nm).

The activatable radionuclide precursor may be associated with the carrier moiety via any suitable means known in the art. For example, the activatable radionuclide precursor may be encapsulated by the carrier moiety as it forms, embedded in the surface of the carrier moiety, attached to the surface of the carrier moiety or conjugated to an individual molecule (e.g., a polymer) prior to its incorporation into the carrier moiety. The activatable radionuclide precursor may be attached to the surface of the carrier moiety directly (e.g., it may be adsorbed to the surface of the carrier moiety or it may form a covalent or non-covalent bond with the surface of the carrier moiety) or indirectly (i.e., one or more linker molecules may be interposed between the surface of the carrier moiety and the activatable radionuclide precursor).

In some embodiments, the carrier moiety comprises one or more targeting agents. For example, the carrier moiety may comprise a tumor-targeting agent, such as a tumor-targeting peptide; a tumor-targeting antibody, antibody fragment, affibody; transferrin or folate. See, e.g., Grifman, MOLEC. THER. 3:964 (2001); Konda et al., INVEST. RADIOL. 35(1):50 (2000); Ojima, ACC. CHEM. RES. 41(1):108 (2008); Qian et al., NATURE BIOTECH. 26:83 (2008).

A targeting agent may be associated with the carrier moiety via any suitable means known in the art. For example, the targeting agent may be encapsulated by the carrier moiety as it forms, embedded in the surface of the carrier moiety, attached to the surface of the carrier moiety or conjugated to an individual molecule (e.g., a polymer) prior to its incorporation into the carrier moiety. The targeting agent may be attached to the surface of the carrier moiety directly (e.g., it may be adsorbed to the surface of the carrier moiety or it may form a covalent or non-covalent bond with the surface of the carrier moiety) or indirectly (i.e., one or more linker molecules may be interposed between the surface of the carrier moiety and the targeting agent).

Radiotherapeutic Agents

The present invention provides radiotherapeutic agents that comprise, consist essentially of or consist of a radionuclide and a carrier moiety. In some embodiments, the radiotherapeutic agent comprises, consists essentially of or consists of radiotherapeutic microparticles and/or radiotherapeutic nanoparticles.

I. Radionuclide

Radiotherapeutic agents of the present invention may comprise any suitable radionuclide known in the art. In some embodiments, the radionuclide comprises, consists essentially of or consists of $^{24}Na$, $^{32}P$, $^{59}Fe$, $^{75}Se$, $^{86}Rb$, $^{89}Sr$, $^{90}Y$, $^{131}I$, $^{140}La$, $^{142}Pr$, $^{153}Sm$, $^{165}Dy$, $^{166}Ho$, $^{169}Er$, $^{176}Lu$, $^{186}Re$, $^{188}Re$, $^{198}Au$, $^{204}Tl$ and/or $^{210}Po$. In some embodiments, the radionuclide comprises, consists essentially of or consists of a radioactive lanthanide isotope. In some embodiments, the radionuclide comprises, consists essentially of or consists of $^{32}P$, $^{89}Sr$, $^{90}Y$, $^{131}I$, $^{140}La$, $^{142}Pr$, $^{153}Sm$, $^{165}Dy$, $^{166}Ho$, $^{169}Er$, $^{176}$Lu, $^{186}$Re and/or $^{188}$Re. In some embodiments, the radionuclide comprises, consists essentially of or consists of $^{166}$Ho.

In some embodiments, the radionuclide comprises, consists essentially of or consists of a radionuclide conjugated to a hydrophobic and/or lipophilic moiety. The radionuclide may be conjugated to any suitable hydrophobic and/or lipophilic moiety known in the art, including, but not limited to, 2,4-pentanedione (acetylacetone), ethyl acetoacetate, 3-methyl-2,4-pentanedione, 3-ethyl-2,4-pentanedione, 2,4-hexanedione and diethyl malonate. In some embodiments, the radionuclide is conjugated to acetylacetonate (e.g., $^{166}$(AcAc)$_3$).

Radionuclides of the present invention may be synthesized via any suitable method known in the art. See, e.g., Bult et al., PHARM. RES. 27:2205 (2010); Mumper et al., J. NUCL. MED. 32(11):2139 (1991); Di Pasqua et al., *Neutron-activatable holmium-containing mesoporous silica nanoparticles as a potential radionuclide therapeutic agent for ovarian cancer*, J. NUCL. MED. in press (2012); Di Pasqua et al., *Tumor accumulation of neutron-activatable holmium-containing mesoporous silica nanoparticles in an orthotopic non-small cell lung cancer mouse model*, INORGANICA CHIMICA ACTA in press (2012); Di Pasqua et al., SMALL 8:997 (2012); Mumper et al., J. NUCL. MED. 33(3):398 (1992); Nijsen et al., EUR. J. NUCL. MED. 26:699 (1999). In some embodiments, the radionuclide is produced via neutron activation of an activatable radionuclide precursor (e.g., an activatable radionuclide precursor of the present invention).

II. Carrier Moieties

Radiotherapeutic agents of the present invention may comprise any suitable carrier moiety known in the art. In some embodiments, the carrier moiety is a micelle (e.g., a polymeric micelle). See, e.g., Aliabadi & Lavasanifar, EXPERT OPIN. DRUG DELIV. 3(1):139 (2006); Croy & Kwon, CURR. PHARM. DES. 12(36):4669 (2006); Kwon, CRIT. REV. THER. DRUG CARRIER MOIETY SYST. 20(5):357 (2003). In some embodiments, the carrier moiety is selected from the group consisting of microporous/mesoporous/macroporous silica particles (including, but not limited to, MCM-41, MCM-48, SBA-15, TUD-1, FSM-16, HMM-1, HMM33, KSW-1, KSW-2 and MSU-1 type silica particles), metallic oxide particles, biocompatible polymer particles, solid lipid particles, polymer-coated nanoparticles, poly(methyl methacrylate) particles, poly(alkyl cyanoacrylate) particles, polyacrylate particles, PS particles, PGA particles, PLA particles, PLGA particles and stearic acid-conjugated pullulan (SAP) particles. See generally U.S. Patent Publication Nos. 2004/0022840 and 2007/0237826; Kim and Oh, ARCH. PHARM. RES. 33:761-767 (2010); Kreuter, J. ANAT. 189:503 (1996); Kwon et al. COLLOID POLYM. SCI. 286:1181 (2008). In some embodiments, the carrier moiety is selected from the group consisting of a polymeric micelle, a solid lipid particle and a mesoporous silica particle. In some embodiments, the carrier moiety is an MCM-41 type mesoporous silica particle or DSPE-PEG). In some embodiments, the carrier moiety is a microparticle or a nanoparticle.

Carrier moieties of the present invention may be synthesized via any suitable method known in the art. See, e.g., U.S. Patent Publication Nos. 2004/0022840 and 2007/0237826; Di Pasqua et al., *Tumor accumulation of neutron-activatable holmium-containing mesoporous silica nanoparticles in an orthotopic non-small cell lung cancer mouse model*, INORGANICA CHIMICA ACTA in press (2012); Kreuter, J. ANAT. 189: 503 (1996). In some embodiments, the carrier moiety is an MCM-41 type mesoporous silica particle synthesized as follows:

1. heat a solution comprising 7 mL 2.0 M NaOH and 480 mL H$_2$O to 80° C.;
2. 2.0 g of cetyltrimethylammonium bromide and 11.3 mL of tetraethyl orthosilicate are added to the solution of step 1, optionally while stirring the solution of step 1, thereby forming a white precipitate;
3. the white precipitate of step 2 is washed with H$_2$O and absolute ethanol prior to being dried in vacuo;
4. 1.0 g of the washed, dried precipitate of step 3 is added to 150 mL absolute ethanol to form a wet precipitate;
5. 0.5 mL of concentrated HCl is added to the wet precipitate of step 4, optionally while stirring the wet precipitate of step 4;
6. the mixture of step 5 is incubated at 50° C. for 5 hours, thereby forming a calcined solid; and
7. the calcined solid of step 6 is washed with H$_2$O and absolute ethanol prior to being dried in vacuo.

In some such embodiments, the MCM-41 type mesoporous silica particles have a diameter of between about 50 nm and about 500 nm (e.g., about 400 nm).

The radionuclide may be associated with the carrier moiety via any suitable means known in the art. For example, the radionuclide may be encapsulated by the carrier moiety as it forms, embedded in the surface of the carrier moiety, attached to the surface of the carrier moiety or conjugated to an individual molecule (e.g., a polymer) prior to its incorporation into the carrier moiety. The activatable radionuclide precursor may be attached to the surface of the carrier moiety directly (e.g., it may be adsorbed to the surface of the carrier moiety or it may form a covalent or non-covalent bond with the surface of the carrier moiety) or indirectly (i.e., one or more linker molecules may be interposed between the surface of the carrier moiety and the activatable radionuclide precursor). In some embodiments, the radionuclide is associated with the carrier moiety from the moment it comes into existence (e.g., the radionuclide is produced by activating an activatable radionuclide precursor that is associated with a carrier moiety).

In some embodiments, the carrier moiety comprises one or more targeting agents. For example, the carrier moiety may comprise a tumor-targeting agent, such as a tumor-targeting peptide; a tumor-targeting antibody, antibody fragment, affibody; transferrin or folate. See, e.g., Grifman, MOLEC. THER. 3:964 (2001); Konda et al., INVEST. RADIOL. 35(1):50 (2000); Ojima, ACC. CHEM. RES. 41(1):108 (2008); Qian et al., NATURE BIOTECH. 26:83 (2008).

A targeting agent may be associated with the carrier moiety via any suitable means known in the art. For example, the targeting agent may be encapsulated by the carrier moiety as it forms, embedded in the surface of the carrier moiety, attached to the surface of the carrier moiety or conjugated to an individual molecule (e.g., a polymer) prior to its incorporation into the carrier moiety. The targeting agent may be attached to the surface of the carrier moiety directly (e.g., it may be adsorbed to the surface of the carrier moiety or it may form a covalent or non-covalent bond with the surface of the carrier moiety) or indirectly (i.e., one or more linker molecules may be interposed between the surface of the carrier moiety and the targeting agent).

Pharmaceutical Compositions

The present invention provides pharmaceutical compositions comprising, consisting essentially of or consisting of a stable activatable particle and/or radiotherapeutic agent and a pharmaceutically acceptable carrier. In some embodiments, the pharmaceutical composition comprises one or more stable activatable particles (e.g., a stable activatable particle of the present invention), which is/are subsequently activated (via neutron activation, for example). In some embodiments, the pharmaceutical composition comprises one or more radiotherapeutic agents (e.g., a radiotherapeutic agent of the present invention).

The pharmaceutical composition may comprise any suitable pharmaceutical carrier moiety, including, but not limited to, phosphate buffered saline and isotonic saline solution. Other examples of pharmaceutically acceptable carriers may be found, for example, in ANSEL'S PHARMACEUTICAL DOSAGE FORMS AND DRUG DELIVERY SYSTEMS (9th Ed., Lippincott Williams and Wilkins (2010)), PHARMACEUTICAL SCIENCES (18th Ed., Mack Publishing Co. (1990) or REMINGTON: THE SCIENCE AND PRACTICE OF PHARMACY (21st Ed., Lippincott Williams & Wilkins (2005)).

The pharmaceutical composition may comprise any suitable diluent or excipient, including, but not limited to, those set forth in ANSEL'S PHARMACEUTICAL DOSAGE FORMS AND DRUG DELIVERY SYSTEMS (9th Ed., Lippincott Williams and Wilkins (2010)), HANDBOOK OF PHARMACEUTICAL EXCIPIENTS (6th Ed., American Pharmaceutical Association (2009)) and REMINGTON: THE SCIENCE AND PRACTICE OF PHARMACY (21st Ed., Lippincott Williams & Wilkins (2005)).

The pharmaceutical composition may comprise any suitable auxiliary substance, including, but not limited to, pH adjusting and/or buffering agents, tonicity adjusting and/or buffering agents and lipid-protective agents that protect lipids against free-radical and lipid-peroxidative damages (e.g., alpha-tocopherol and water-soluble iron-specific chelators, such as ferrioxamine).

The pharmaceutical composition may be formulated so as to be suitable for administration via any known method, including, but not limited to, oral, intravenous (i.v.), subcutaneous, intramuscular, intrathecal, intraperitoneal (i.p.), intrarectal, intravaginal, intranasal, intragastric, intratracheal, sublingual, transcutaneous and intrapulmonary. In some embodiments, the composition is formulated for intraperitoneal injection or intravenous injection.

The concentration of stable activatable particle and/or radiotherapeutic agent in the pharmaceutical composition may vary widely (i.e., from less than about 0.05% to about 90% or more by weight) in accordance with the particular mode of administration, the disease(s)/disorder(s)/symptom(s) being treated, the age/weight of the subject, etc.

Methods

The present invention provides methods of producing stable activatable particles and radiotherapeutic agents and methods of providing radiotherapy to subjects in need thereof.

A first aspect of the present invention is a method of producing a stable activatable particle, comprising, consisting essentially of or consisting of incorporating/conjugating an activatable radionuclide precursor into/to a carrier moiety.

A further aspect of the present invention is a method of producing a radiotherapeutic agent, comprising, consisting essentially of or consisting of activating a stable activatable particle of the present invention.

A further aspect of the present invention is a method of treating a disorder in a subject in need thereof, comprising, consisting essentially of or consisting of administering to said subject a therapeutically effective amount of a radiotherapeutic agent and/or a pharmaceutical composition of the present invention.

Producing a Stable Activatable Particle

The present invention provides methods of producing a stable activatable particle, comprising, consisting essentially of or consisting of incorporating/conjugating an activatable radionuclide precursor into/to a carrier moiety. In some embodiments, the activatable radionuclide precursor may be incorporated into/conjugated to a carrier moiety to produce a stable activatable particle having a diameter of about 0.5 nm to about 1 µm. For example, an activatable radionuclide precursor may be incorporated into/conjugated to a carrier moiety to form a stable activatable particle having a diameter of about 5 nm to about 100 nm.

Any suitable method known in the art may be used to incorporate/conjugate an activatable radionuclide precursor into/to a carrier moiety. For example, the activatable radionuclide precursor may be encapsulated by the carrier moiety as it forms, embedded in the surface of the carrier moiety, attached to the surface of the carrier moiety or conjugated to an individual molecule (e.g., a polymer) prior to its incorporation into the carrier moiety. The activatable radionuclide precursor may be attached to the surface of the carrier moiety directly (e.g., it may be adsorbed to the surface of the carrier moiety or it may form a covalent or non-covalent bond with the surface of the carrier moiety) or indirectly (i.e., one or more linker molecules may be interposed between the surface of the carrier moiety and the activatable radionuclide precursor).

Any suitable activatable radionuclide precursor known in the art may be conjugated to a carrier moiety. In some embodiments, the activatable radionuclide precursor comprises, consists essentially of or consists of $^{23}$Na, $^{31}$P, $^{56}$Fe, $^{74}$Se, $^{85}$Rb, $^{88}$Sr, $^{89}$Y, $^{127}$I, $^{152}$Sm, $^{164}$Dy, $^{165}$Ho, $^{168}$Er, $^{175}$Lu, $^{197}$Au and/or $^{203}$Tl. In some embodiments, the activatable radionuclide precursor comprises, consists essentially of or consists of a stable lanthanide isotope that may be converted into a radioactive lanthanide isotope (via neutron activation, for example). In some embodiments, the activatable radionuclide precursor comprises, consists essentially of or consists of $^{31}$P, $^{88}$Sr, $^{89}$Y, $^{127}$I, $^{149}$Sm, $^{150}$Sm, $^{152}$Sm, $^{164}$Dy, $^{165}$Ho, $^{168}$Er and/or $^{175}$Lu. In some embodiments, the activatable radionuclide precursor comprises, consists essentially of or consists of $^{165}$Ho. In some embodiments, the activatable radionuclide precursor is hydrophobic and/or lipophilic (e.g., $^{165}$Ho(AcAc)$_3$).

The activatable radionuclide precursor may be conjugated to any suitable carrier moiety. In some embodiments, the carrier moiety is a micelle (e.g., a polymeric micelle). See, e.g., Aliabadi & Lavasanifar, EXPERT OPIN. DRUG DELIV. 3(1): 139 (2006); Croy & Kwon, CURR. PHARM. DES. 12(36):4669 (2006); Kwon, CRIT. REV. THER. DRUG CARRIER MOIETY SYST. 20(5):357 (2003). In some embodiments, the carrier moiety is selected from the group consisting of microporous/mesoporous/macroporous silica particles (including, but not limited to, MCM-41, MCM-48, SBA-15, TUD-1, FSM-16, HMM-1, HMM33, KSW-1, KSW-2 and MSU-1 type silica particles), metallic oxide particles, biocompatible polymer particles, solid lipid particles, polymer-coated nanoparticles, poly(methyl methacrylate) particles, poly(alkyl cyanoacrylate) particles, polyacrylate particles, PS particles, PGA particles, PLA particles, PLGA particles and stearic acid-conjugated pullulan (SAP) particles. See generally U.S. Patent Publication Nos. 2004/0022840 and 2007/0237826; Kim and Oh, ARCH. PHARM. RES. 33:761-767 (2010); Kreuter, J. ANAT. 189: 503 (1996); Kwon et al. COLLOID POLYM. SCI. 286:1181 (2008). In some embodiments, the carrier moiety is selected from the group consisting of a polymeric micelle, a solid lipid particle and a mesoporous silica particle. In some embodiments, the carrier moiety is an MCM-41 type mesoporous silica particle or DSPE-PEG. In some embodiments, the carrier moiety is an MCM-41 type mesoporous silica particle synthesized as follows:

1. heat a solution comprising 7 mL 2.0 M NaOH and 480 mL $H_2O$ to 80° C.;
2. 2.0 g of cetyltrimethylammonium bromide and 11.3 mL of tetraethyl orthosilicate are added to the solution of step 1, optionally while stirring the solution of step 1, thereby forming a white precipitate;
3. the white precipitate of step 2 is washed with $H_2O$ and absolute ethanol prior to being dried in vacuo;
4. 1.0 g of the washed, dried precipitate of step 3 is added to 150 mL absolute ethanol to form a wet precipitate;
5. 0.5 mL of concentrated HCl is added to the wet precipitate of step 4, optionally while stirring the wet precipitate of step 4;
6. the mixture of step 5 is incubated at 50° C. for 5 hours, thereby forming a calcined solid; and
7. the calcined solid of step 6 is washed with $H_2O$ and absolute ethanol prior to being dried in vacuo.

In some such embodiments, the MCM-41 type mesoporous silica particles have a diameter of about 400 nm.

In some embodiments, the activatable radionuclide precursor is hydrophobic and/or lipophilic and the carrier moiety is selected from the group consisting of a polymeric micelle, a solid lipid particle and a mesoporous silica particle. Because hydrophobic and/or lipophilic activatable radionuclide precursors may be readily conjugated to polymeric micelles, solid lipid nanoparticles and mesoporous silica particles, such a combination may result in a significant increase in the amount of activatable radionuclide precursor that is loaded into/onto the carrier moiety. For example, conjugating a hydrophobic and/or lipophilic activatable radionuclide precursor to a carrier moiety selected from the group consisting of a polymeric micelle, a solid lipid particle and a mesoporous silica particle may increase the amount of activatable radionuclide precursor that is loaded into the carrier moiety by at least 1%, 2%, 3%, 4%, 5%, 10%, 15%, 20%, 25%, 30%, 35%, 40%, 45%, 50%, 60%, 70%, 80%, 90%, 100%, 125%, 150%, 175%, 200%, 250% or more as compared to an activatable radionuclide precursor that is neither hydrophobic nor lipophilic.

In some embodiments, the carrier moiety comprises one or more targeting agents. For example, the carrier moiety may comprise a tumor-targeting agent, such as a tumor-targeting peptide; a tumor-targeting antibody, antibody fragment, affibody; transferrin or folate. See, e.g., Grifman, MOLEC. THER. 3:964 (2001); Konda et al., INVEST. RADIOL. 35(1):50 (2000); Ojima, ACC. CHEM. RES. 41(1):108 (2008); Qian et al., NATURE BIOTECH. 26:83 (2008).

A targeting agent may be associated with the carrier moiety via any suitable means known in the art. For example, the targeting agent may be encapsulated by the carrier moiety as it forms, embedded in the surface of the carrier moiety, attached to the surface of the carrier moiety or conjugated to an individual molecule (e.g., a polymer) prior to its incorporation into the carrier moiety. The targeting agent may be attached to the surface of the carrier moiety directly (e.g., it may be adsorbed to the surface of the carrier moiety or it may form a covalent or non-covalent bond with the surface of the carrier moiety) or indirectly (i.e., one or more linker molecules may be interposed between the surface of the carrier moiety and the targeting agent).

Producing a Radiotherapeutic Agent

The present invention provides methods of producing a radiotherapeutic agent, comprising, consisting essentially of or consisting of producing a stable activatable particle according to a method of the present invention and activating the stable activatable particle. In some embodiments, the stable activatable particle comprises, consists essentially of or consists of a hydrophobic and/or lipophilic activatable radionuclide precursor and a carrier moiety selected from the group consisting of a polymeric micelle, a solid lipid particle and a mesoporous silica particle. In some embodiments, the stable activatable particle comprises, consists essentially of or consists of $^{165}Ho(AcAc)_3$ and the carrier moiety comprises, consists essentially of or consists of an MCM-41 type mesoporous silica particle or DSPE-PEG.

Any suitable method known in the art may be used to activate the stable activatable particle, including, but not limited to, neutron activation. See, e.g., Bult et al., PHARM. RES. 27:2205 (2010); Mumper et al., J. NUCL. MED. 32(11):2139 (1991); Mumper et al., J. NUCL. MED. 33(3):398 (1992). Neutron activation is an attractive approach for producing radiotherapeutic agents because it allows for the manufacture of carrier moiety systems that are non-radioactive during the preparation, transport and storage phases of the process, thereby allowing for the carrier moiety system to be optimized without the time constraints and usual hazards associated with handling the large amounts of radioactivity usually required for internal radiation therapy. It is anticipated that neutron-activated nanoparticles will improve the clinical outcome for cancer patients, particularly after intraperitoneal administration to patients suffering from peritoneal carcinomatosis, the primary cause of morbidity and mortality in women with ovarian cancer.

Treating a Disorder

The present invention provides methods of treating a disorder responsive to radiotherapeutic agents in a subject in need thereof, comprising, consisting essentially of or consisting of administering to said subject a therapeutically effective amount of a radiotherapeutic agent and/or a pharmaceutical composition of the present invention. In some embodiments, the radiotherapeutic agent comprises, consists essentially of or consists of a hydrophobic and/or lipophilic radionuclide and a carrier moiety selected from the group consisting of a polymeric micelle, a solid lipid particle and a mesoporous silica particle. In some embodiments, the hydrophobic and/or lipophilic radionuclide comprises, consists essentially of or consists of $^{166}Ho(AcAc)_3$ and the carrier moiety comprises, consists essentially of or consists of an MCM-41 type mesoporous silica particle or DSPE-PEG.

The radiotherapeutic agent may be administered using any suitable method known in the art, including, but not limited to, oral, intravenous (i.v.), subcutaneous, intramuscular, intrathecal, intraperitoneal (i.p.), intrarectal, intravaginal, intranasal, intragastric, intratracheal, intratumoral, sublingual, transcutaneous and intrapulmonary. In some embodiments, the radiotherapeutic agent is administered via intraperitoneal injection. In some embodiments, the radiotherapeutic agent is injected directly into a tumor.

Methods of the present invention may be used to treat any suitable disorder known in the art, including, but not limited to, cancer, trigeminal neuralgia, severe thyroid eye disease, pterygium, pigmented villonodularsynovitis, vascular restenosis, heterotopic ossification and rheumatoid arthritis, synovial osteochondromatosis, synovial chondromatosis and hemathrosis. In some embodiments, the disorder is a hematological cancer, such as acute myeloid leukemia, chronic myeloid leukemia, hairy cell leukemia, lymphoblastic leukemia, lymphocytic leukemia, AIDS-related lymphoma, Burkitt's lymphoma, cutaneous T-Cell lymphoma, Hodgkin lymphoma, Non-Hodgkin lymphoma, primary central nervous system lymphoma or myeloma. In some embodiments, the disorder is a solid cancer, such as anal cancer, basal cell carcinoma, bile duct cancer, bladder cancer, bone cancer, brain cancer (e.g., cerebellar astrocytoma, ependymoma, glioma, medulloblastoma, neuroblastoma, etc.), breast cancer (e.g., metastatic breast cancer), cervical cancer, colon cancer, endometrial cancer, esophageal cancer, eye cancer (e.g., intraocular melanoma, retinoblastoma, etc.), gallbladder cancer, gastrointestinal cancer, heart cancer, kidney cancer (e.g., renal cell carcinoma), laryngeal cancer, lip cancer, liver cancer, lung cancer (e.g., non-small cell lung cancer, small cell lung cancer, etc.), melanoma, mesothelioma, oral cancer, ovarian cancer, pancreatic cancer, parathyroid cancer, peritoneal carcinomatosis, pharyngeal cancer, prostate cancer, rectal cancer, skin cancer (e.g., Merkel cell carcinoma, squamous cell carcinoma, etc.), stomach cancer, throat cancer, thyroid cancer, urethral cancer, uterine cancer, vaginal cancer or vulvar cancer.

EXAMPLES

The following examples are not intended to be a detailed catalogue of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

Example 1

Selecting a Suitable Activatable Radionuclide Precursor

When we were considering neutron-activatable nuclei for inclusion in stable activatable particles of the present invention, we were guided by the basic neutron activation equation:

$$A = nf\sigma(1-e^{-\lambda T})e^{-\lambda t} \quad \text{Equation 1}$$

where A=radioactivity produced (disintegrations/s; dps), n=number of target atoms, f=neutron flux density (n/cm²·s), σ=thermal neutron capture cross section (cm²; 1 barn=$10^{-24}$ cm²), λ=decay constant ($0.693/t_{1/2}$), T=irradiation time and t=decay time. In addition, we considered the toxicity of the element to be included in the carrier moiety system. Because lanthanides are non-toxic and relatively easy to form into hydrophobic complexes, and because several of the lanthanides have relatively large thermal neutron capture cross sections, we chose to investigate their potential efficacy further.

In our efforts to determine which neutron-activatable nuclei may be most appropriate for inclusion in stable activatable particles of the present invention, we have developed an equation to determine the neutron irradiation time required to produce therapeutically equivalent amounts of radiation. The "Therapeutically Equivalent Factor" (TEF) is calculated using the natural abundance and isotopic mass of the stable isotope in the carrier moiety, the thermal neutron capture cross section of this stable isotope, the irradiation time required to reach maximum production of the radioactive isotope $(1-e^{-\lambda T})$, which is dependent on the half-life of the radioactive isotope ($t_{1/2}=\lambda/0.693$), and the radiation dose delivered by the radioactive isotope. Thus, $$TEF = \frac{[\text{Natural Abundance (\%)}][\sigma(cm^2)]}{[\text{Isotopic Mass (g/mole)}]} \quad \text{Equation 2}$$

The TEF values of a number of stable isotopes and their corresponding radioactive neutron-activated product isotopes; including isotopes of Y, Rh, Pr, Pm, Dy, Ho, Lu, and Re were calculated. The greatest TEF value belonged to the activation of $^{164}$Dy to $^{165}$Dy. However, the half-life of $^{165}$Dy (2.3 h) was deemed too short to be of practical value. For the purposes of the following examples, we selected the isotope pair with the next highest TEF value, $^{165}$Ho/$^{166}$Ho, based on its 100% natural abundance, high neutron capture cross-section (64 barns), reasonable half-life (26.8 h), high beta energy ($E_{max}$=1.84 MeV), high potential absorbed radiation dose (10 mGy/MBq), and the fact that it emits low yield (6.6%) 81 keV photons that can be imaged with a planar or SPECT camera.

Example 2

Preparation of Stable Activatable Particles Comprising $^{165}$Ho $^{165}$Ho(AcAc)$_3$ was prepared by adding 2,4-pentanedione to holmium (III) chloride aqueous solution, and the pH was adjusted to 7.5 with ammonium hydroxide. The solution was stirred at room temperature for four hours, and the precipitate was collected via filtration and washed with water.

Stable activatable particles comprising $^{165}$Ho-$^{165}$Ho-MCM-41 nanoparticles—were prepared by exposing MCM-41 type mesoporous silica particles (10 mg) to $^{165}$Ho(AcAc)$_3$ (0.5 mg/mL) in 15 mL water and stirring vigorously for 24 hours at room temperature. The $^{165}$Ho-MCM-41 nanoparticles were retrieved by centrifugation (1,300×g for 20 minutes), washed twice with water and dried (in vacuo for 24 hours). Inductively coupled plasma-mass spectrometry (ICP-MS) indicated that the $^{165}$Ho content of the $^{165}$Ho-MCM-41 nanoparticles was 17.8±1.4% w/w. TEM indicated that the $^{165}$Ho-MCM-41 nanoparticles were approximately 80-100 nm in diameter. The zeta potential of the $^{165}$Ho-MCM-41 nanoparticles in water, as measured using a Zetasizer Nano ZS (Malvern Instruments Ltd., Malvern, Worcestershire, UK), was −49.2±6.0 mV.

Example 3

Neutron Activation of Stable Activatable Particles Comprising $^{165}$Ho $^{165}$Ho-MCM-41 nanoparticles (Example 2) were irradiated in a 1-MW pool-type nuclear reactor (PULSTAR, North Carolina State University, Raleigh, N.C.) with a thermal neutron flux of approximately 5.5×10$^{12}$ n/cm²·s for 1-4 or 18 hours to produce $^{166}$Ho-MCM-41 nanoparticles by neutron capture through a (n,γ) reaction.

The high holmium content of the $^{165}$Ho-MCM-41 nanoparticles made it possible to produce $^{166}$Ho-MCM-41 nanoparticles with significant levels of radioactivity. In some instances, the radioactivity of the $^{166}$Ho-MCM-41 nanoparticles was in the range of about 100 to about 500 µCi per 1 mg of material. For example, in one particular set of experiments, irradiation of 10.7 mg of $^{165}$Ho-MCM-41 nanoparticles in a thermal neutron flux of approximately 5.5×10$^{12}$ n/cm$^2$·s for 2.2 hours yielded 3.5 mCi of $^{166}$Ho.

A 2470 Wizard Automatic Gamma Counter (PerkinElmer Inc., Waltham, Mass.) was calibrated using a traceable point source (National Institute of Standards and Technology (NIST), U.S. Department of Commerce, Gaithersburg, Md.) and used to measure the $^{166}$Ho content of the $^{166}$Ho-MCM-41 nanoparticles by quantifying the 81 keV photons emitted by $^{166}$Ho. The $^{166}$Ho content of the $^{166}$Ho-MCM-41 nanoparticles was about 20% w/w. For example, in one set of experiments, the $^{166}$Ho content of the $^{166}$Ho-MCM-41 nanoparticles was 17.8±1.4% w/w.

To determine how much $^{166}$Ho was retained in the $^{166}$Ho-MCM-41 nanoparticles after irradiation and handling, suspensions containing 4 mg/mL of $^{166}$Ho-MCM-41 nanoparticles in PBS, pH 7.4, were passed through a molecular weight filter immediately or after incubation at 37° C. for 24 hours. $^{166}$Ho radioactivity in the filtrate was measured using a 2470 Wizard Automatic Gamma Counter (PerkinElmer Inc., Waltham, Mass.). As shown in FIG. 1, the $^{166}$Ho-MCM-41 nanoparticles retained approximately 100% of their initial $^{166}$Ho despite being diluted 10- or 100-fold and remained stable after being incubated at 37° C. for 24 hours.

Example 4

$^{166}$Ho-MCM-41 Nanoparticles Accumulate in Tumors

SKOV-3 ovarian tumor mice were prepared by injecting approximately 7×10$^6$ SKOV-3 human ovarian tumor cells into the peritoneal cavity of athymic (nu/nu) mice. Following a two-month incubation period, magnetic resonance imaging (MRI) was used to visualize the resultant tumors.

SKOV-3 ovarian tumor mice with intraperitoneal metastasis were intraperitoneally injected with ≤5 mg of $^{166}$Ho-MCM-41 nanoparticles (Example 3; approximately 650 µCi) or an equivalent amount of $^{166}$Ho(AcAc)$_3$ (approximately 650 µCi) in 300 µL 1% carboxymethylcellulose (CMC) in PBS, pH 7.4.

Figure 2:
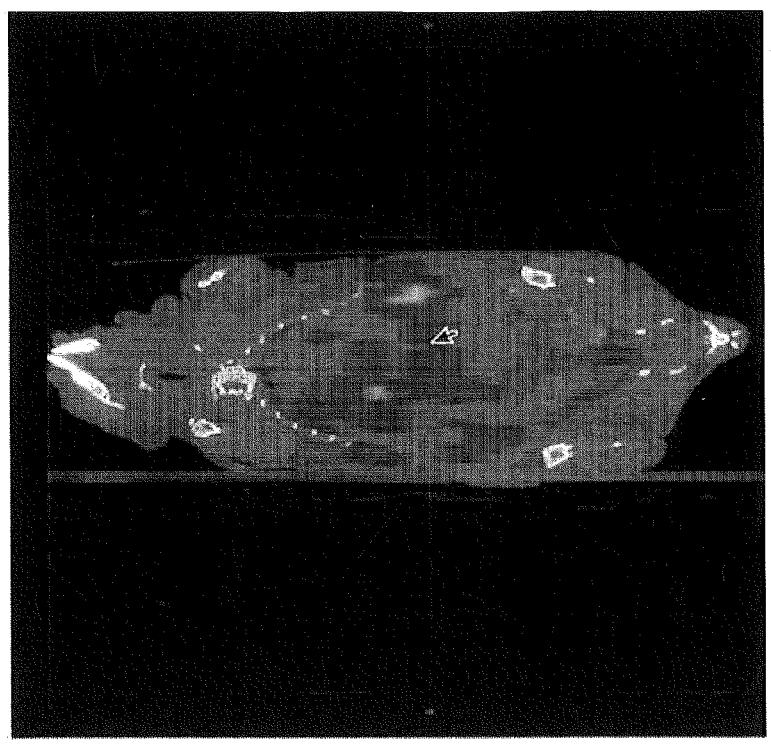
FIG. 2A, 2B show that intraperitoneally injected $^{166}$Ho-MCM-41 nanoparticles accumulated in the tumors of mice injected with SKOV-3 human ovarian tumor cells.
Figure 2:
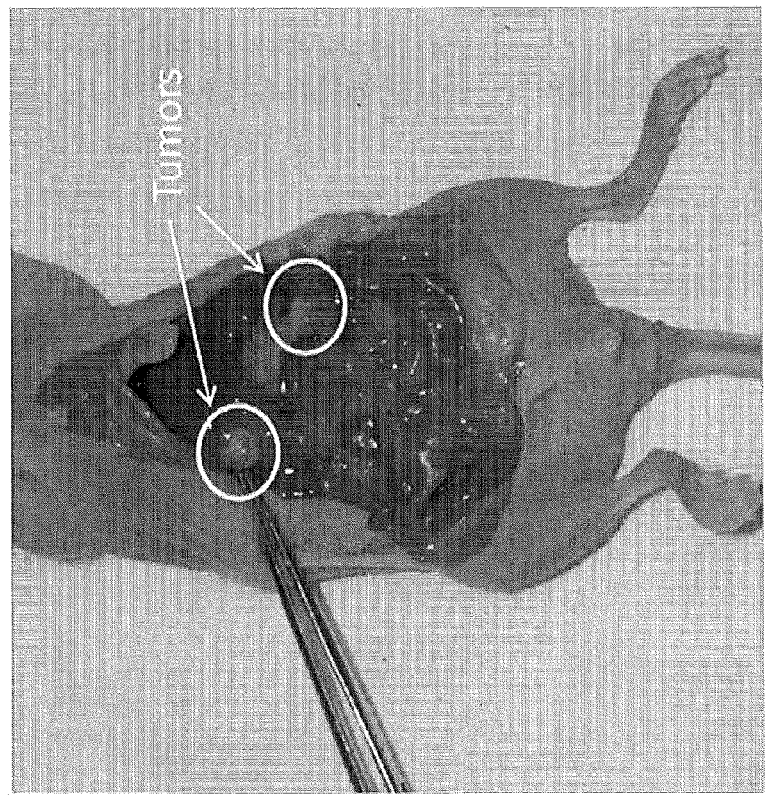

SPECT/CT images acquired one hour after injection using an eXplore speCZt™ system (GE Healthcare) with a mouse multi-slit collimator and reconstructed using a 70-90 keV energy window to detect 81 keV photons emitted by the $^{166}$Ho. As shown in FIGS. 2A, 2B, the $^{166}$Ho-MCM-41 nanoparticles predominantly accumulated in tumors.

Figure 3:
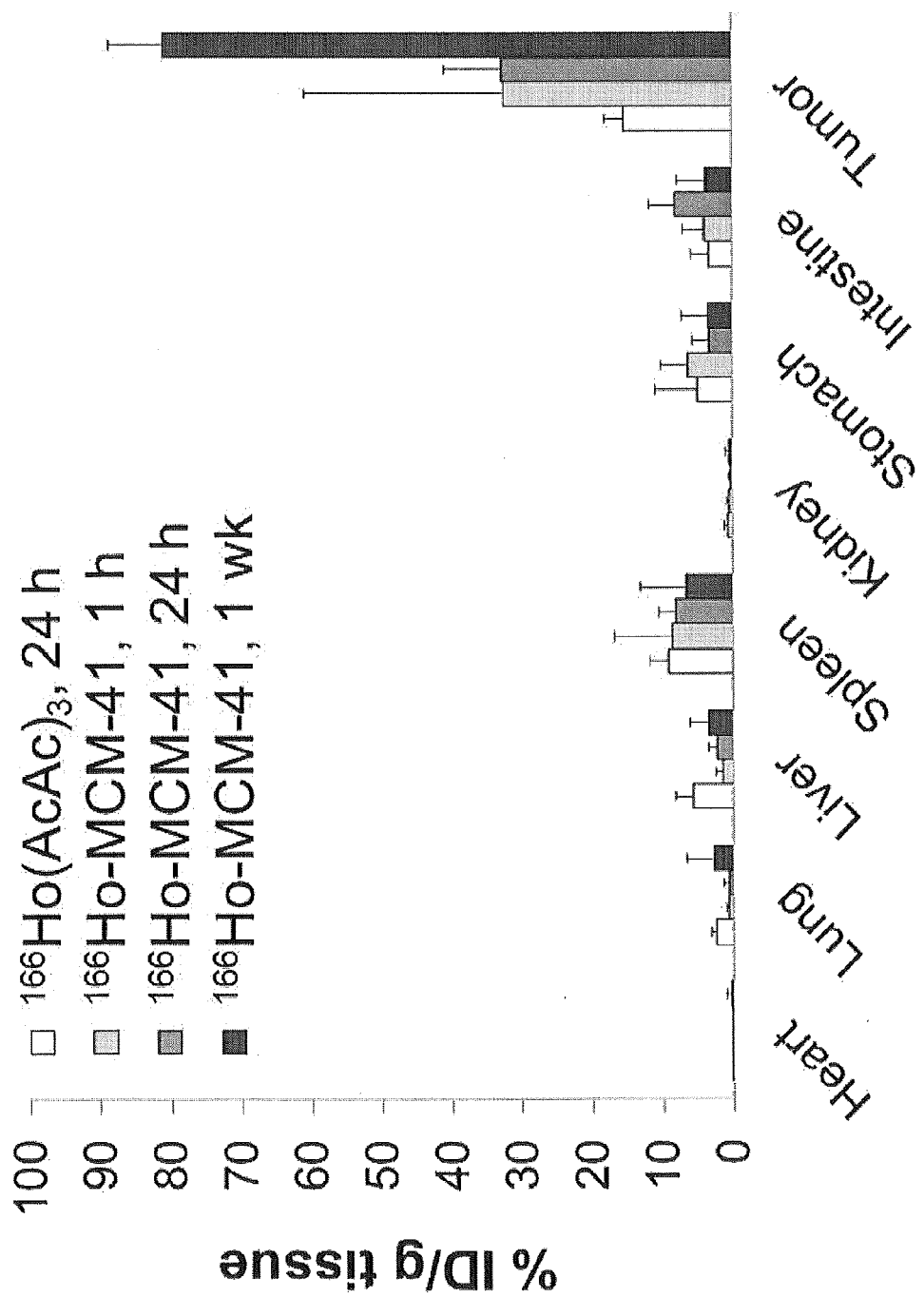
FIG. 3 is a graph that shows the biodistribution of $^{166}$Ho following intraperitoneal injection of $^{166}$Ho-MCM-41 nanoparticles or $^{166}$Ho(AcAc)$_3$ in SKOV-3 ovarian tumor mice with intraperitoneal metastasis. "$^{166}$Ho(AcAc)$_3$, 24 h" represents data acquired 24 hours after injection with $^{166}$Ho(AcAc)$_3$. "$^{166}$Ho-MCM-41, 1 h" represents data acquired one hour after injection with $^{166}$Ho-MCM-41 nanoparticles. "$^{166}$Ho-MCM-41, 24 h" represents data acquired 24 hours after injection with $^{166}$Ho-MCM-41 nanoparticles. "$^{166}$HoMCM-41, 1 wk" represents data acquired one week after injection with $^{166}$Ho-MCM-41 nanoparticles.

Biodistribution studies were performed one hour, 24 hours and one week after injection by removing and weighing various organs from mice that were injected with $^{166}$Ho-MCM-41 nanoparticles and mice that were injected with $^{166}$Ho(AcAc)$_3$ and quantifying the $^{166}$Ho content of each organ using a 2470 Wizard Automatic Gamma Counter (PerkinElmer Inc., Waltham, Mass.). FIG. 3. After 24 hours, 32.8±8.1 percent initial dose per gram (% ID/g) was measured in tumors of mice injected with $^{166}$Ho-MCM-41 nanoparticles, which is two times that measured in the tumors of mice injected with $^{166}$Ho(AcAc)$_3$ (15.4±2.7% ID/g). Moreover, 81.0±7.5% ID/g of the $^{166}$Ho-MCM-41 nanoparticles had accumulated in tumors after 1 week, greater than 12 times that in any other organ (i.e., liver, spleen).

Figure 4:
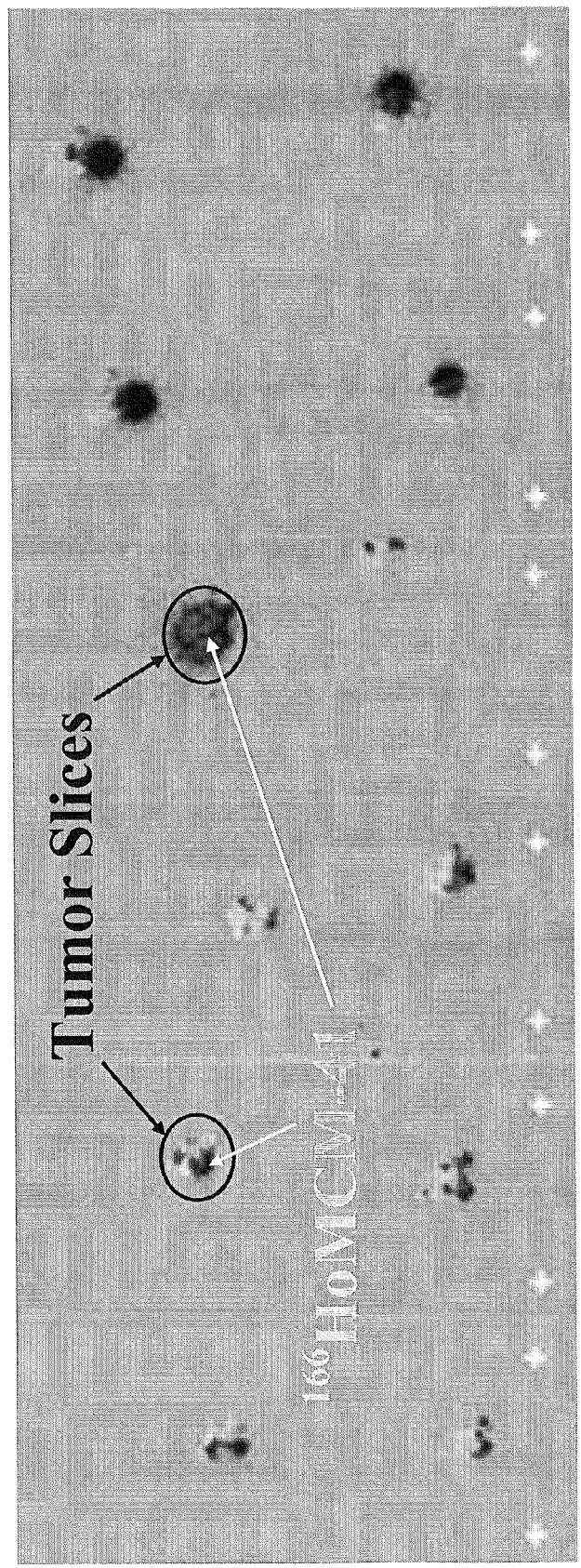
FIG. 4 is an autoradiograph that shows $^{166}$Ho distribution in tumor slices acquired from SKOV-3 ovarian tumor mice with intraperitoneal metastasis 24 hours after intraperitoneal injection with $^{166}$Ho-MCM-41 nanoparticles.

To investigate the spatial distribution of $^{166}$Ho within the tumors, autoradiographic images of tumor slices were superimposed on photographs of the tumor slices. FIG. 4. Tumors that were removed from mice 24 hours after i.p. injection with $^{166}$Ho-MCM-41 nanoparticles were sliced using a Leica CM1850 cryostat (Leica Microsystems Nussloch GmbH, Nussloch, Germany). Autoradiographs of tumor slices were prepared using storage phosphor screens (GE Healthcare) and a Cyclone Plus Phosphor Imager (PerkinElmer, Inc., Waltham, Mass.). As shown in FIG. 4, $^{166}$Ho-MCM-41 nanoparticles diffused throughout many of the tumors over the 24-hour period following injection.

Example 5

$^{166}$Ho-MCM-41 Nanoparticles Reduce Tumor Volume

SKOV-3 ovarian tumor mice were prepared by injecting approximately 7×10$^6$ SKOV-3 human ovarian tumor cells into the peritoneal cavity of athymic (nu/nu) mice. Following a two-month incubation period, magnetic resonance imaging (MRI) was used to visualize the resultant tumors.

SKOV-3 ovarian tumor mice with intraperitoneal metastasis were intraperitoneally injected with 2 mg of $^{165}$Ho-MCM-41 nanoparticles (Example 2) or $^{166}$Ho-MCM-41 nanoparticles (Example 3; approximately 110 µCi) in 200 µL of 1% CMC in PBS, pH 7.4.

Figure 5A:
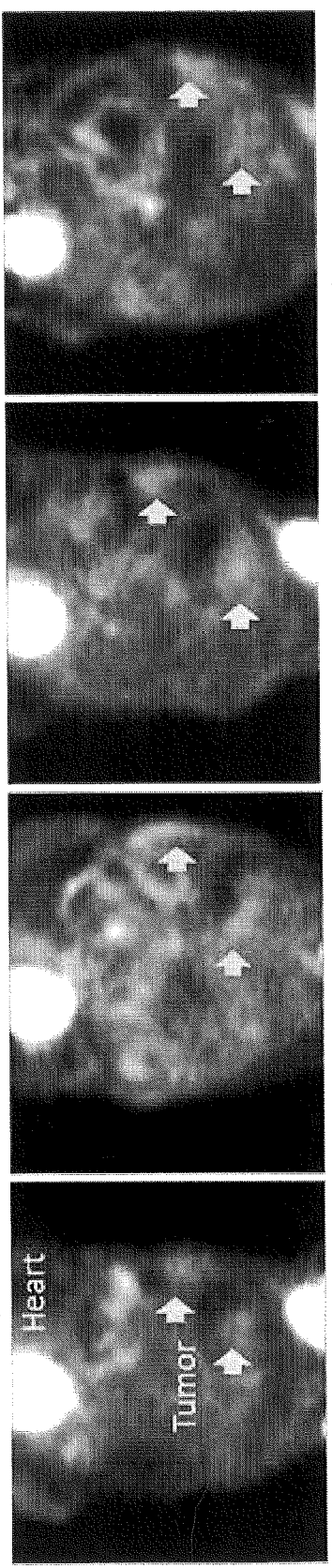
FIGS. 5A, 5B show that intraperitoneal injection of $^{166}$Ho-MCM-41 nanoparticles reduced tumor size in SKOV-3 ovarian tumor mice with intraperitoneal metastasis.
Figure 5A:
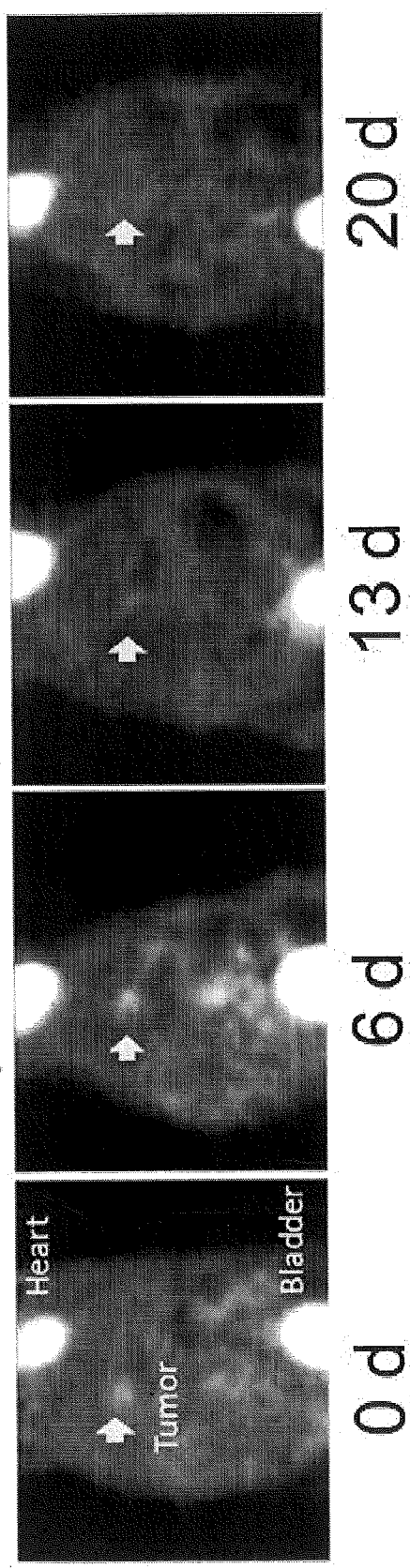
Figure 5B:
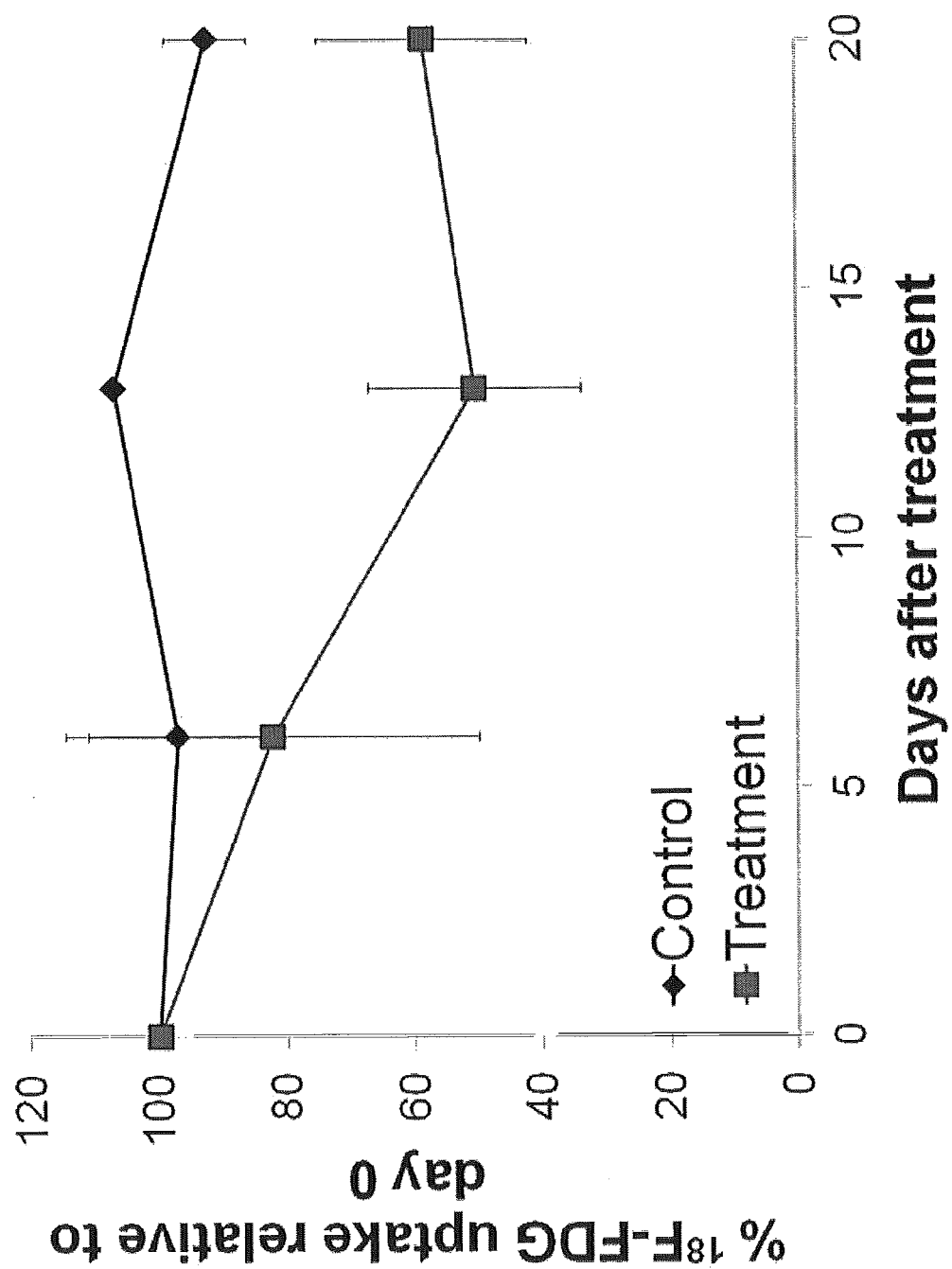

Tumor growth was monitored in vivo using PET/CT following intravenous administration of the radio-fluorinated glucose analog $^{18}$F-FDG. FIGS. 5A, 5B. Prior to injection (day zero) and six, 13 and 20 days after injection with the $^{165}$Ho-MCM-41 or $^{166}$Ho-MCM-41 nanoparticles, the mice were anesthetized with isoflurane (1.5%) mixed with oxygen and intravenously injected with 200 µCi of $^{18}$F-FDG via the tail vein. Mice were kept warm on a heating pad before being moved to the PET/CT scanner. Thirty minutes after $^{18}$F-FDG injection, static PET image acquisition commenced. PET image acquisition continued for 10 minutes. Images were reconstructed using 2D OSEM algorithms with scatter correction, random correction and attenuation correction. A standardized uptake value (SUV) was calculated based on the calibrated counts, the injection dose and animal body weight. Images were analyzed using the region of interest (ROI)-based method. For each animal, tumor regions were manually labeled at similar anatomical positions at each time point. The maximum SUV in the ROI at various time points relative to that at day zero was calculated as the percent $^{18}$F-FDG uptake. As shown in FIG. 5B, the SUV associated with $^{18}$F-FDG uptake in tumors of mice treated with $^{166}$Ho-MCM-41 nanoparticles significantly decreased over time (p<0.05), indicating that the active tumor volume of mice treated with $^{166}$Ho-MCM-41 nanoparticles was significantly reduced over the course of the 20-day observation period. The SUV associated with $^{18}$F-FDG uptake in tumors of mice treated with $^{165}$Ho-MCM-41 nanoparticles did not appreciably change over the 20-day observation period, indicating that treatment with $^{165}$Ho-MCM-41 nanoparticles had no effect on active tumor volume.

Example 6

$^{166}$Ho-MCM-41 Nanoparticles Reduce Morbidity

SKOV-3 ovarian tumor mice were prepared by injecting approximately 15×10$^6$ SKOV-3 human ovarian tumor cells into the peritoneal cavity of athymic (nu/nu) mice.

Twenty days after implantation, SKOV-3 ovarian tumor mice were intraperitoneally injected with 0.333 mg $^{165}$Ho-MCM-41 nanoparticles (Example 2), 0.333 mg of $^{166}$Ho-MCM-41 nanoparticles (Example 3; 108.7 µCi) or 0.133 mg $^{166}$Ho(AcAc)$_3$ (108.7 µCi) in 400 µL of 1% CMC in PBS, pH 7.4 (n=12 mice per treatment group). An additional 14 SKOV-3 ovarian tumor mice received no treatment and served as the control group. Mice were euthanized if weight loss greater than 10% occurred over a 3 day period, if cumulative weight loss exceeded 20% or if tumor growth interfered with mobility (e.g., if a mouse displayed obvious ascites).

Figure 6:
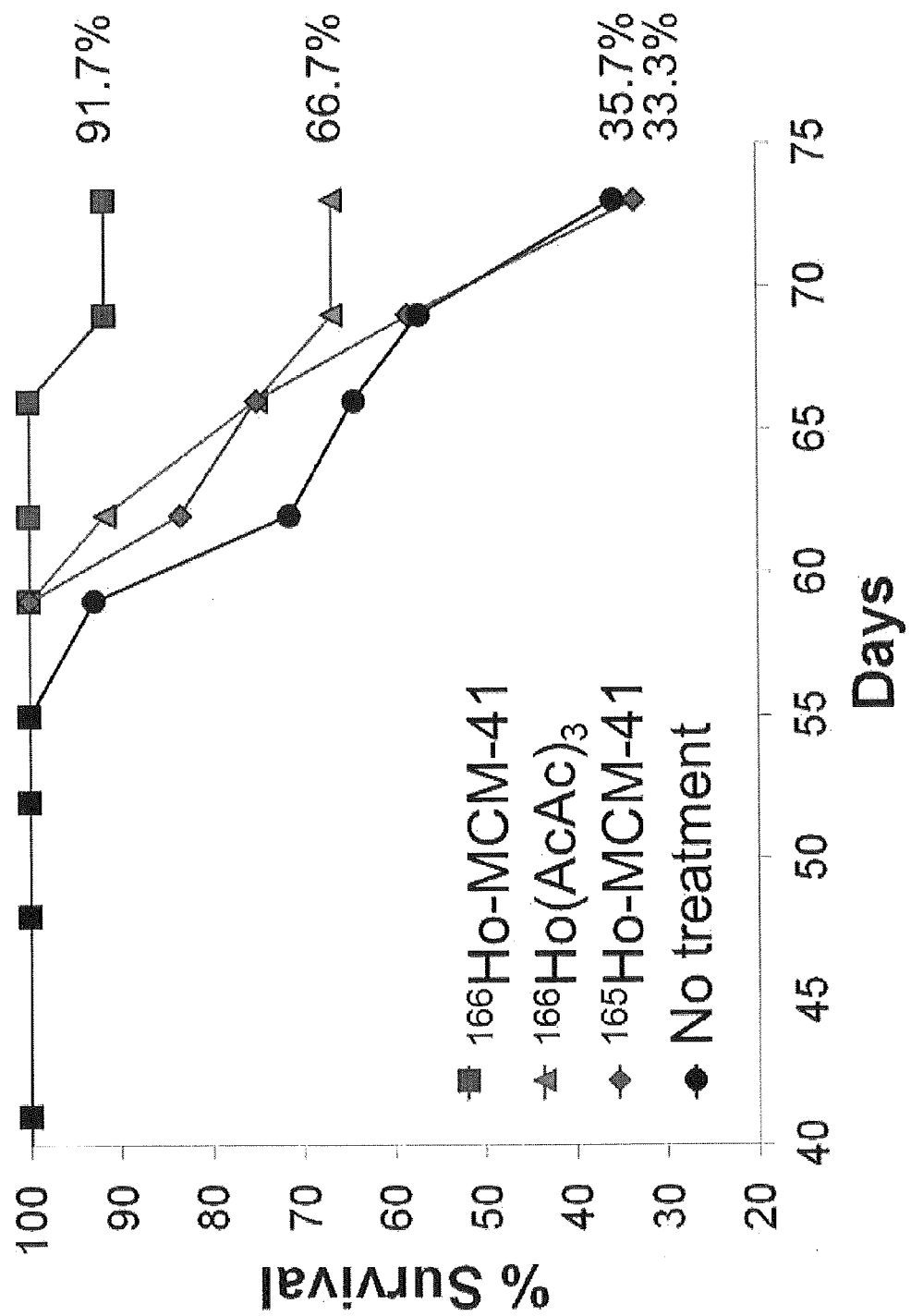
FIG. 6 shows that intraperitoneal injection of $^{166}$Ho-MCM-41 nanoparticles significantly reduced morbidity in SKOV-3 ovarian tumor mice with intraperitoneal metastasis. "$^{166}$Ho-MCM-41" represents mice injected with $^{166}$Ho-MCM-41 nanoparticles twenty days after implantation of SKOV-3 human ovarian tumor cells. "$^{166}$Ho(AcAc)$_3$" represents mice injected with $^{166}$Ho(AcAc)$_3$ twenty days after implantation of SKOV-3 human ovarian tumor cells. "$^{165}$Ho-MCM-41" represents mice injected with $^{165}$Ho-MCM-41 nanoparticles twenty days after implantation of SKOV-3 human ovarian tumor cells. "No treatment" represents mice that received no holmium-containing injection following implantation of SKOV-3 human ovarian tumor cells.

Statistical analyses were performed to compare the fraction of mice that survived over the course of the 73-day period following implantation. The number of surviving animals was greatest in the group injected with $^{166}$Ho-MCM-41 nanoparticles (91.7%), followed by the group injected with $^{166}$Ho(AcAc)$_3$ (66.7%), the control group (35.7%) and the group injected with $^{165}$Ho-MCM-41 nanoparticles (33.3%). FIG. 6. The survival rate of mice injected with $^{166}$Ho-MCM-41 nanoparticles was significantly higher than that of mice in the control group and mice injected with $^{165}$Ho-MCM-41 nanoparticles (p=0.005).

Example 7

Preparation of Stable Activatable Particles Comprising $^{165}$Ho

Figure 7:
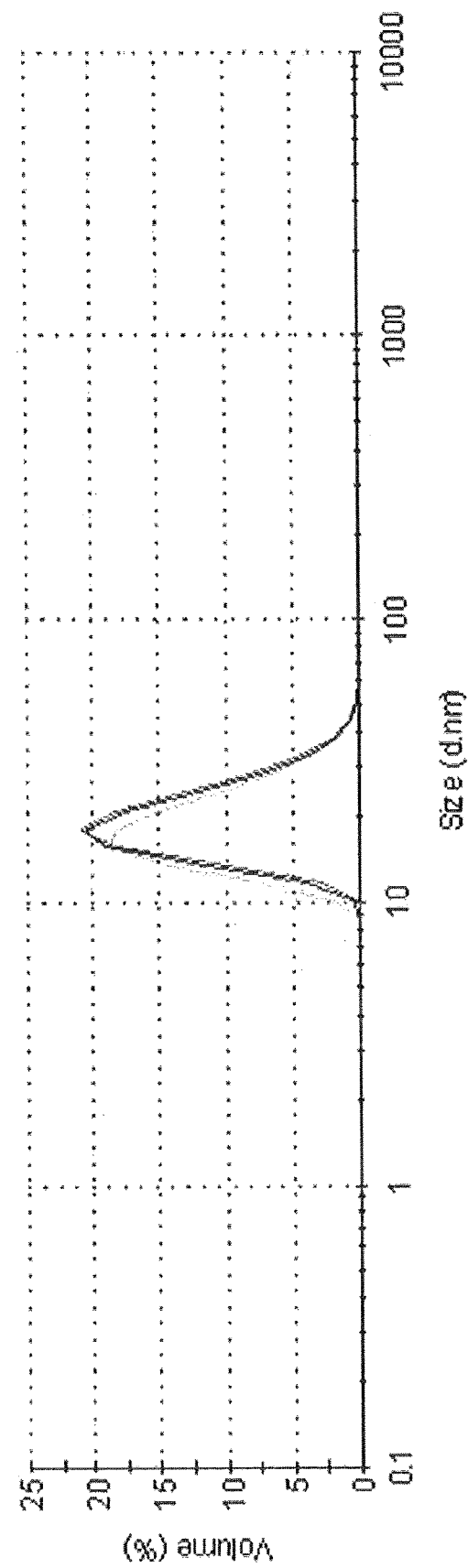
FIG. 7 is a dynamic light scattering graph of $^{165}$Ho-DSPE nanoparticles.
Figure 8:
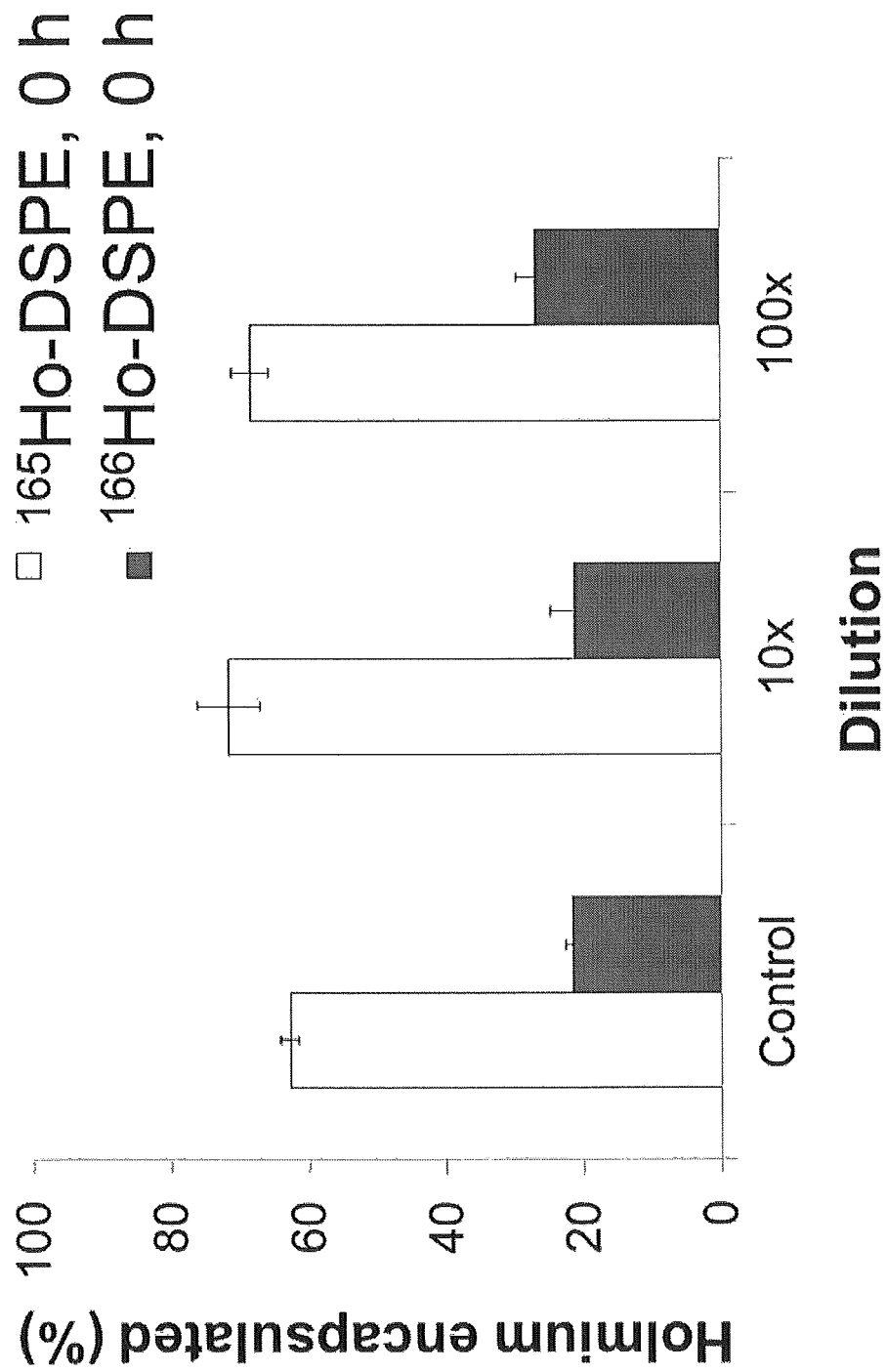
FIG. 8 shows that a radiotherapeutic agent of the present invention ($^{166}$Ho-DSPE nanoparticles) retained a significant portion of its radionuclide ($^{166}$Ho) following dilution. White bars represent data acquired prior to neutron activation. Gray bars present data acquired immediately following neutron activation and dilution in phosphate buffered saline (PBS), pH 7.4.

Stable activatable particles comprising 165Ho-$^{165}$Ho-DSPE nanoparticles—were prepared by exposing 1,2-distearyol-sn-glycero-3-phosphoethanolamine-N-[methoxy (polyethylene glycol)-3000] (DSPE-PEG3000) to $^{165}$Ho (AcAc)$_3$ in a microemulsion. DSPE-PEG3000 (6 mg/mL) and $^{165}$Ho(AcAc)$_3$ (4 mg/mL) were initially combined in an oil film. Water (75° C.) was added and the mixture was stirred for 50 minutes at 70° C. to produce a microemulsion, which was subsequently cooled to 25° C. and filtered to retrieve the $^{165}$Ho-DSPE nanoparticles. The $^{165}$Ho-DSPE nanoparticles had a mean size of 24.2±1.9 nm. FIG. 7. The zeta potential of the $^{165}$Ho-DSPE nanoparticles in water, as measured using a Zetasizer Nano ZS (Malvern Instruments Ltd., Malvern, Worcestershire, UK), was −0.17±0.57 mV. The encapsulation efficiency of the $^{165}$Ho-DSPE nanoparticles was 62.8±1.3%, and the amount of $^{165}$Ho in each nanoparticle remained stable in the face of 10- or 100-fold dilutions. FIG. 8.

Example 8

Figure 9:
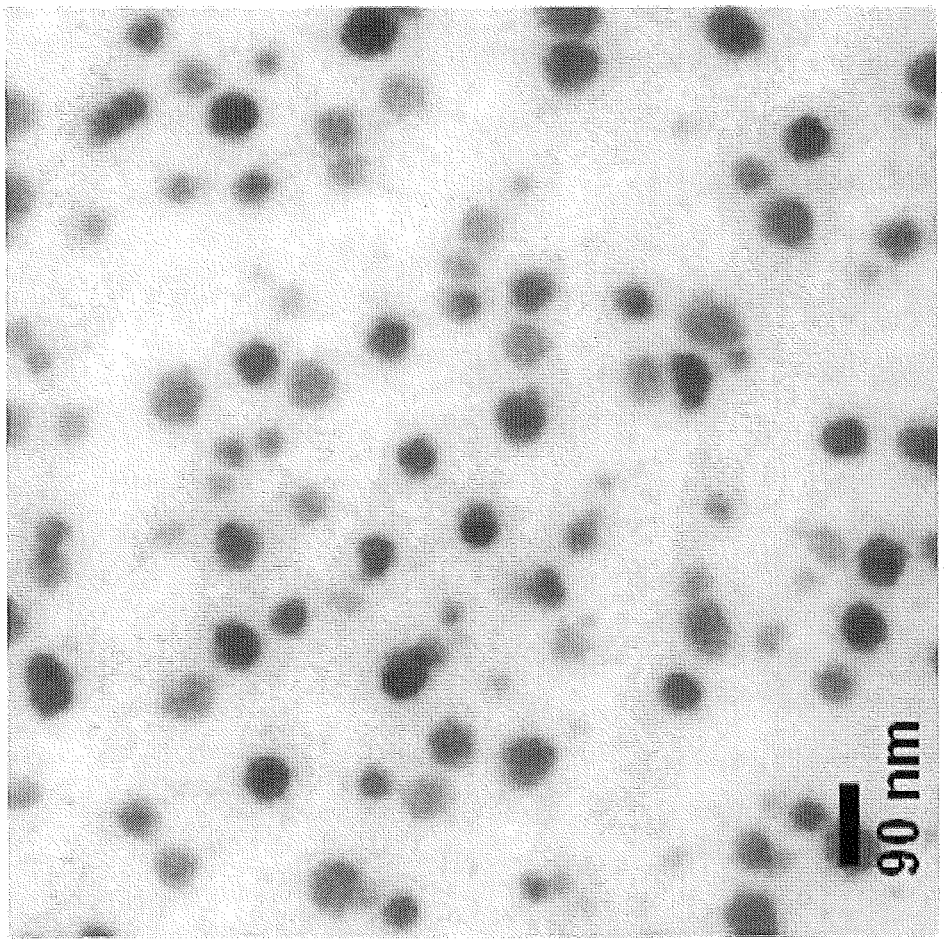
FIG. 9 is a transmission electron microscopy (TEM) image of a radiotherapeutic agent of the present invention ($^{166}$Ho-DSPE nanoparticles).

Neutron Activation of Stable Activatable Particles Comprising $^{165}$Ho $^{165}$Ho-DSPE nanoparticles (Example 7) were irradiated in a 1-MW pool-type nuclear reactor (PULSTAR, North Carolina State University, Raleigh, N.C.) with a thermal neutron flux of approximately $5.5 \times 10^{12}$ n/cm$^2$·s for 13 minutes to produce $^{166}$Ho-DSPE nanoparticles with an activity of approximately 6 µCi/mg. TEM indicated that the $^{166}$Ho-DSPE nanoparticles were intact and that the particles had increased in size (approximately 50 nm) following irradiation. FIG. 9. Following irradiation, 21.5±1.2% of the nanoparticles' initial holmium content was retained and was stable following 10- or 100-fold dilution. FIG. 8.

Example 9

$^{166}$Ho-DSPE Nanoparticles Accumulate in Tumors

SKOV-3 ovarian tumor mice were prepared by injecting approximately $7 \times 10^6$ SKOV-3 human ovarian tumor cells into the peritoneal cavity of athymic (nu/nu) mice. Following a two-month incubation period, magnetic resonance imaging (MRI) was used to visualize the resultant tumors.

SKOV-3 ovarian tumor mice with intraperitoneal metastasis were intraperitoneally injected with $^{166}$Ho-DSPE nanoparticles (Example 8; approximately 125 µCi).

SPECT/CT images were acquired 1 hour and 24 hours after injection to ensure that no radioactivity was leaking out of the peritoneal cavity.

Biodistribution studies were performed 24 hours after injection by removing various organs from the mice and quantifying the $^{166}$Ho content of each organ using a 2470 Wizard Automatic Gamma Counter (PerkinElmer Inc., Waltham, Mass.). 15.04±6.23 percent initial dose per gram (% ID/g) was measured in the tumors.

Example 10

Preparation of Folate-Targeted $^{166}$Ho-DSPE Nanoparticles $^{166}$Ho-DSPE nanoparticles were prepared as described above in Examples 7 and 8, except that 1,2-distearoyl-sn-glycero-3-phosphoethanolamine-N-[folate(polyethylene glycol)-5000] (DSPE-PEG5000-folate) was added during the preparation of the initial emulsion. The formulation contained 4 mg/mL $^{165}$Ho(AcAc)$_3$, 5.4 mg/mL DSPE-PEG3000 and 0.9 mg/mL DSPE-PEG5000-folate.

Example 11

Folate-Targeting Increases Tumor Uptake of $^{166}$Ho-DSPE Nanoparticles In Vitro SKOV-3 human ovarian tumor cells at ~80% confluency in 10 cm culture dishes were incubated with 15 µl (2.2 µCi) of $^{166}$Ho-DSPE nanoparticles (Example 8) or folate-targeted $^{166}$Ho-DSPE nanoparticles (Example 10).

Figure 10:
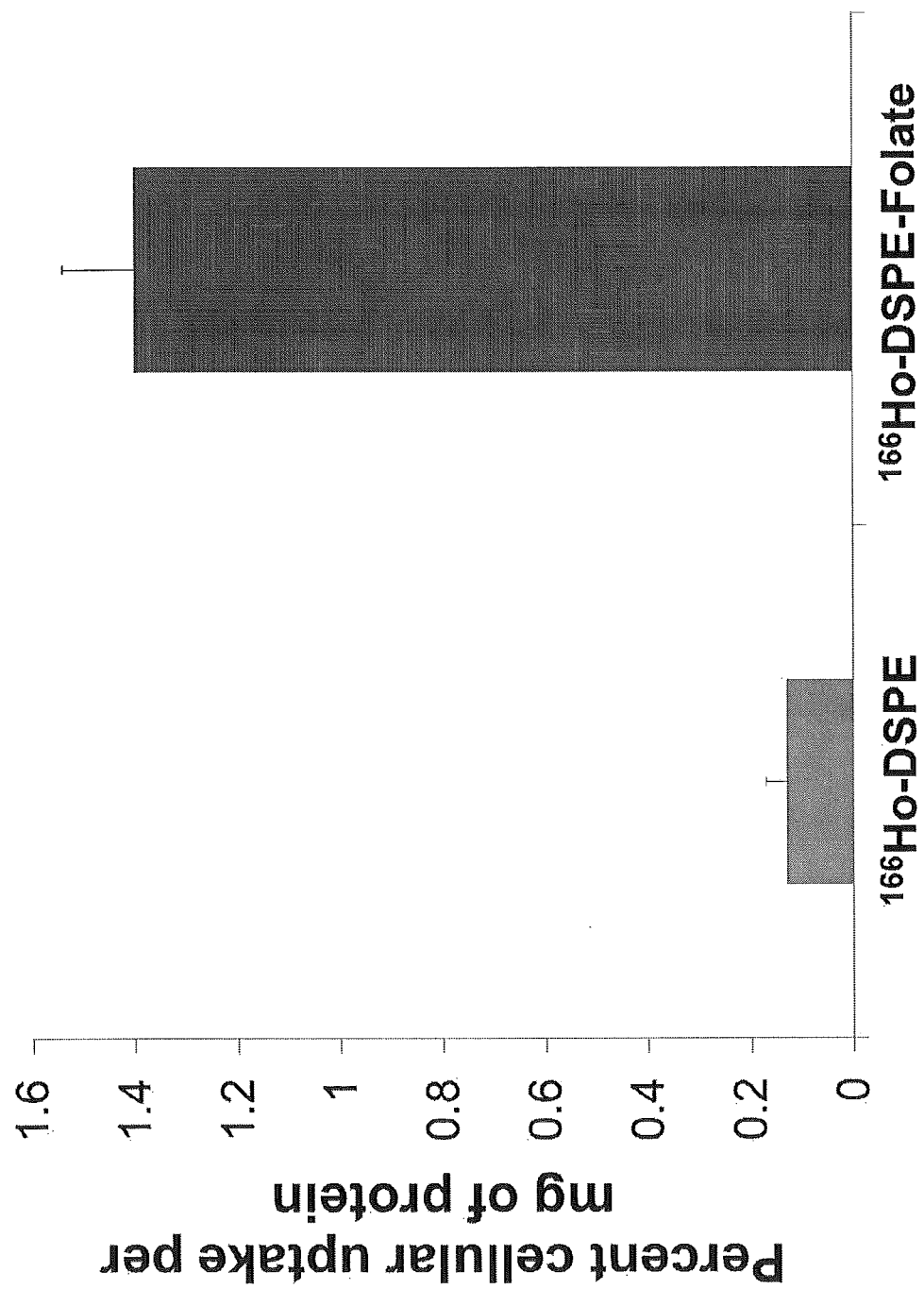
FIG. 10 is a graph that shows the uptake of $^{166}$Ho-DSPE nanoparticles and folate-targeted $^{166}$Ho-DSPE nanoparticles by SKOV-3 ovarian tumor cells in vitro. "$^{166}$Ho-DSPE" represents data acquired from cells exposed to $^{166}$Ho-DSPE nanoparticles. "$^{166}$Ho-DSPE-Folate" represents data acquired from cells exposed to folate-targeted $^{166}$Ho-DSPE nanoparticles.
Figure 11:
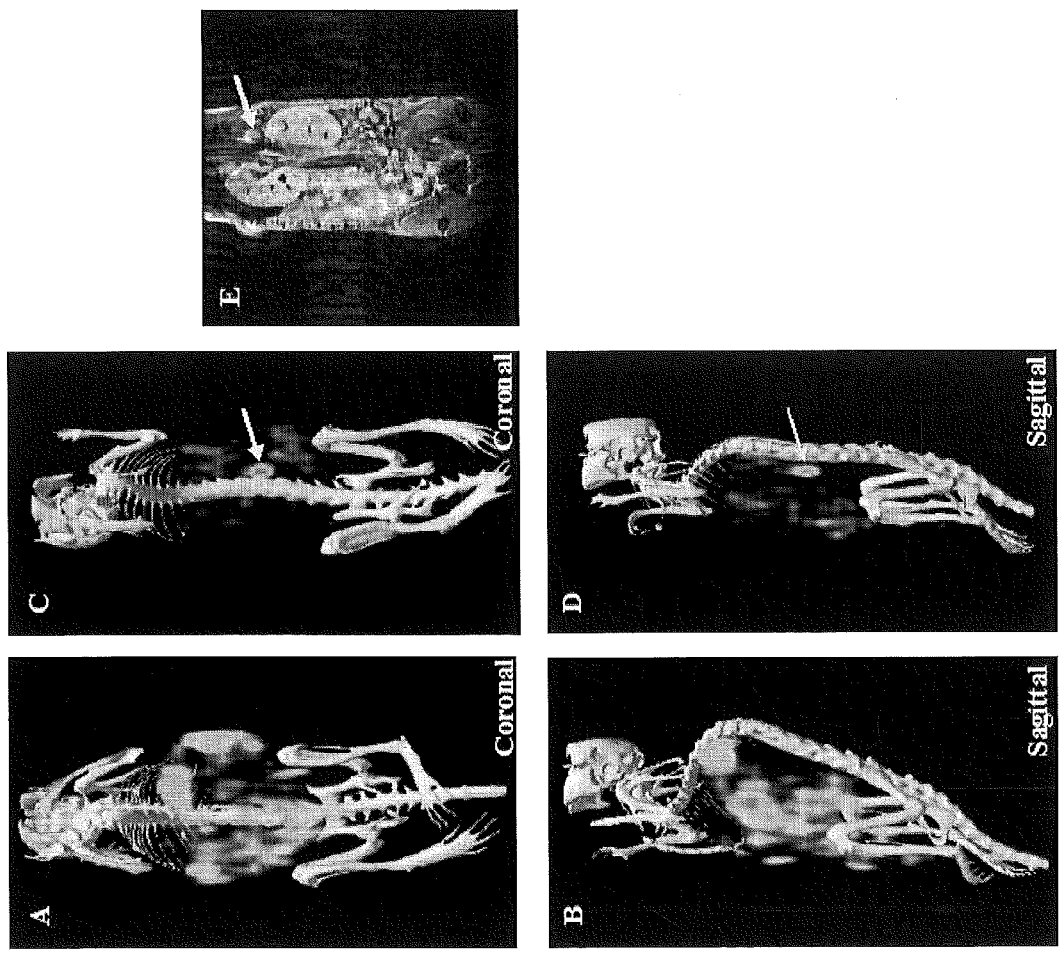
FIGS. 11A-11E show that intraperitoneally injected $^{166}$Ho-DSPE nanoparticles accumulated in the tumors of mice injected with SKOV-3 human ovarian tumor cells.

After 2 hours, uptake of $^{166}$Ho-DSPE nanoparticles was only 0.13±0.04 percent per mg of cell protein, whereas uptake of folate-targeted $^{166}$Ho-DSPE nanoparticles was 1.40±0.14 percent per mg of cell protein. FIG. 10.

Example 12

Folate-Targeted $^{166}$Ho-DSPE Nanoparticles Accumulate in Tumors

SKOV-3 ovarian tumor mice were prepared by injecting approximately $7 \times 10^6$ SKOV-3 human ovarian tumor cells into the peritoneal cavity of athymic (nu/nu) mice. Following a two-month incubation period, magnetic resonance imaging (MRI) was used to visualize the resultant tumors.

SKOV-3 ovarian tumor mice with intraperitoneal metastasis were intraperitoneally injected with $^{166}$Ho-DSPE nanoparticles (Example 8; approximately 125 µCi), folate-targeted $^{166}$Ho-DSPE nanoparticles (Example 10; approximately 125 µCi) or an equivalent amount of $^{166}$Ho (AcAc)$_3$.

SPECT/CT images acquired 1 hour and 24 hours after injection with folate-targeted $^{166}$Ho-DSPE nanoparticles confirmed that the majority of radioactivity remained in the peritoneal cavity. FIGS. 11A-11D.

Figure 12:
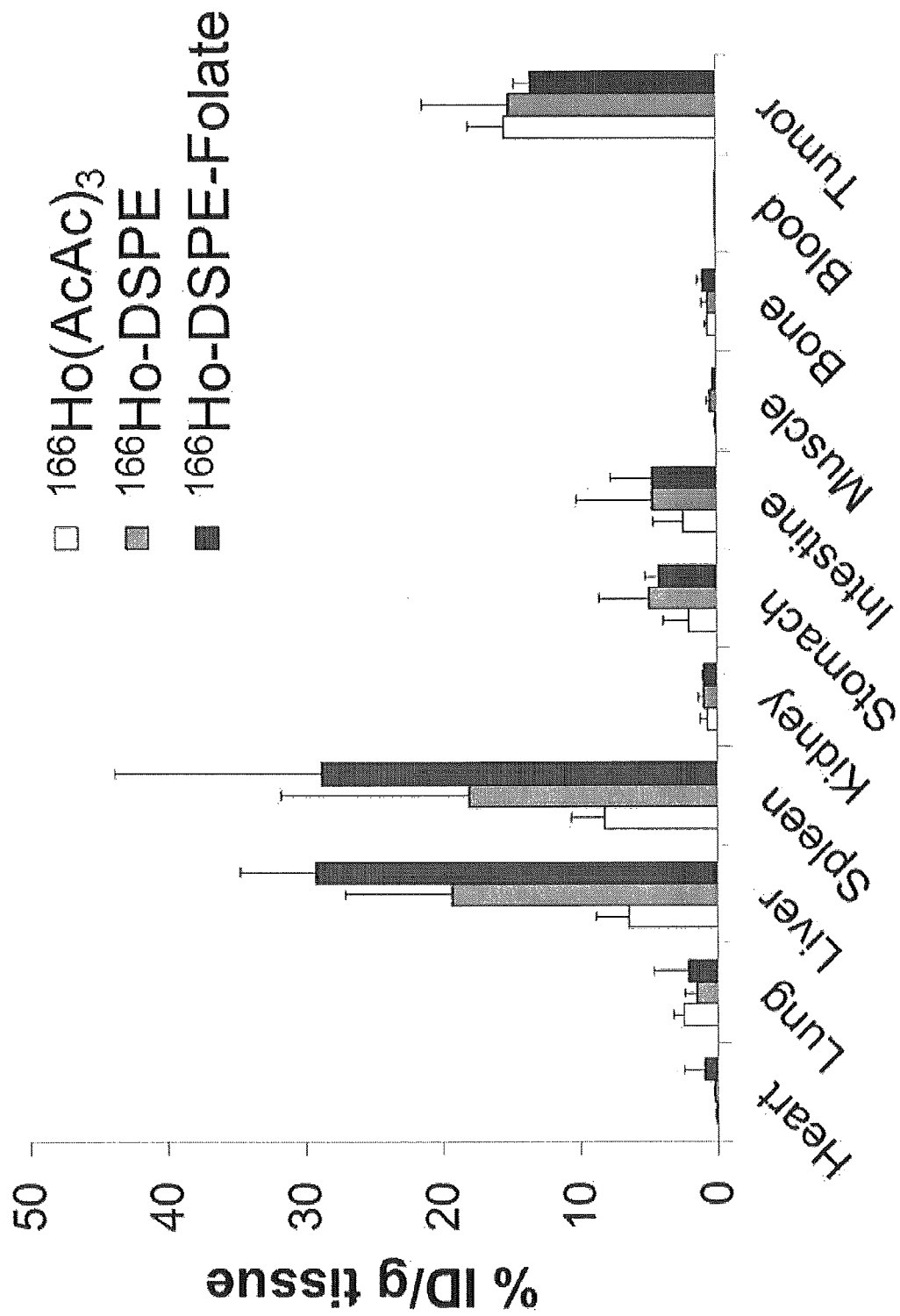
FIG. 12 is a graph that shows the biodistribution of folate-targeted $^{166}$Ho-DSPE nanoparticles, $^{166}$Ho-DSPE nanoparticles and $^{166}$Ho(AcAc)$_3$ 24 hours after intraperitoneal injection in SKOV-3 ovarian tumor mice with intraperitoneal metastasis. "$^{166}$Ho(AcAc)$_3$" represents data acquired 24 hours after injection with $^{166}$Ho(AcAc)$_3$. "$^{166}$Ho-DSPE" represents data acquired 24 hours after injection with $^{166}$Ho-DSPE nanoparticles. "$^{166}$Ho-DSPE-Folate" represents data acquired 24 hours after injection with folate-targeted $^{166}$Ho-DSPE nanoparticles.

Biodistribution studies were performed 24 hours after injection by removing various organs from the mice and quantifying the $^{166}$Ho content of each organ using a 2470 Wizard Automatic Gamma Counter (PerkinElmer Inc., Waltham, Mass.). 13.46±1.16 percent initial dose per gram (% ID/g) was measured in the tumors of mice injected with folate-targeted $^{166}$Ho-DSPE nanoparticles. FIG. 12.

Example 13

Preparation of Stable Activatable Particles Comprising $^{165}$Ho $^{165}$Ho(AcAc)$_3$ was prepared by adding 2,4-pentanedione to holmium (III) chloride aqueous solution, and the pH was adjusted to 7.5 with ammonium hydroxide. The solution was stirred at room temperature for four hours, and the precipitate was collected via filtration and washed with water.

Figure 13:
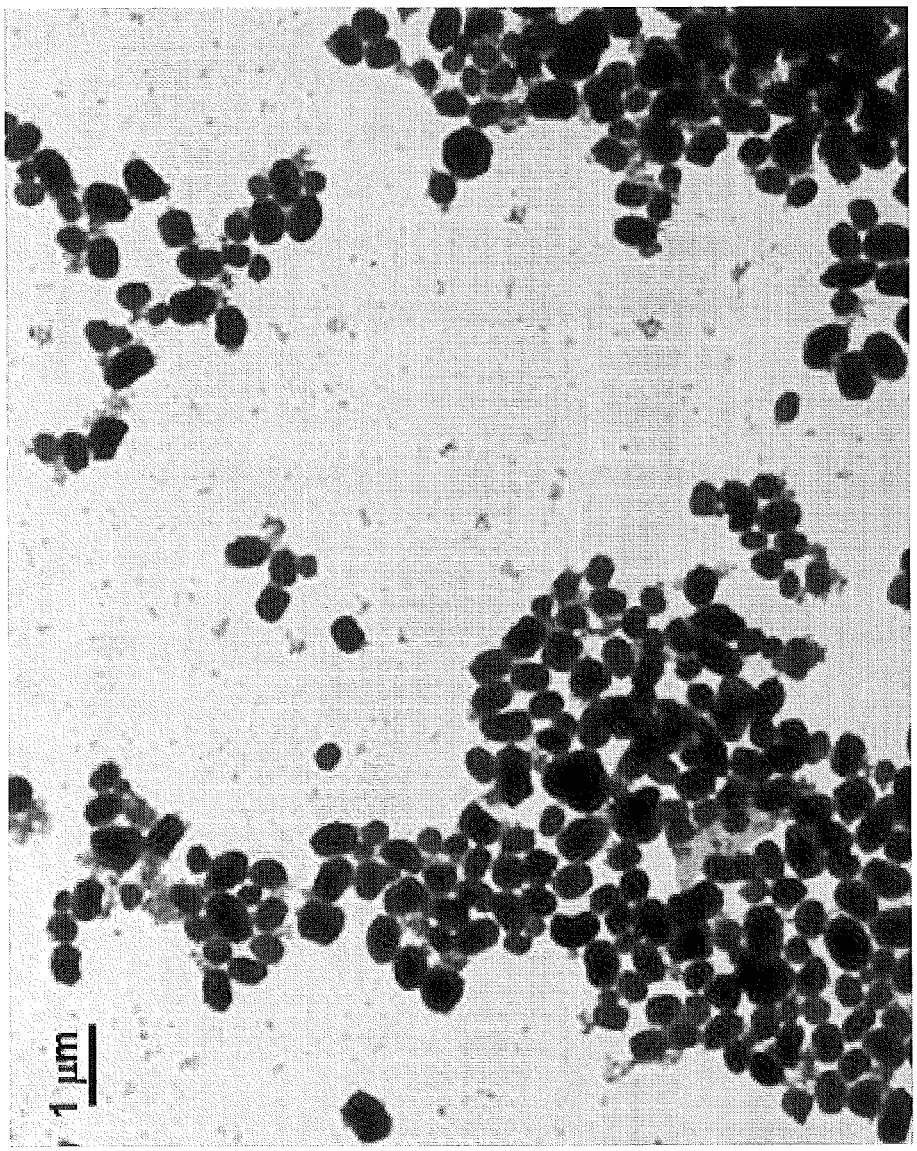
FIG. 13 is a TEM image of MCM-41 nanoparticles.

Stable activatable particles comprising $^{165}$Ho-$^{165}$Ho-MCM-41 nanoparticles—were prepared by exposing MCM-41 type mesoporous silica particles (10 mg) to $^{165}$Ho(AcAc)$_3$ (0.5 mg/mL) in 15 mL water and stirring vigorously for 24 hours at room temperature. TEM indicated that the MCM-41 type mesoporous silica particles were approximately 400 nm in diameter. FIG. 13. The $^{165}$Ho-MCM-41 nanoparticles were retrieved by centrifugation (1,300×g for 20 minutes), washed twice with water and dried (in vacuo for 24 hours).

Example 14

Neutron Activation of Stable Activatable Particles Comprising $^{165}$Ho $^{165}$Ho-MCM-41 nanoparticles (Example 13) were irradiated in a 1-MW pool-type nuclear reactor (PULSTAR, North Carolina State University, Raleigh, N.C.) with a thermal neutron flux of approximately 5.5×10$^{12}$ n/cm$^2$·s or 7.7×10$^{12}$ n/cm$^2$·s for 2-3 hours to produce $^{166}$Ho-MCM-41 nanoparticles by neutron capture through a (n,γ) reaction.

The high holmium content of the $^{165}$Ho-MCM-41 nanoparticles made it possible to produce $^{166}$Ho-MCM-41 nanoparticles with significant levels of radioactivity. In some instances, the radioactivity of the $^{166}$Ho-MCM-41 nanoparticles was in the range of about 100 to about 500 μCi per 1 mg of material. For example, in one particular set of experiments, irradiation of $^{165}$Ho-MCM-41 nanoparticles in a thermal neutron flux of approximately 5.5×10$^{12}$ n/cm$^2$·s for 2 hours yielded 150 μCi of $^{166}$Ho in 1 mg of $^{166}$Ho-MCM-41 nanoparticles. Similarly, in one set of experiments, irradiation of $^{165}$Ho-MCM-41 nanoparticles in a thermal neutron flux of approximately 7.7×10$^{12}$ n/cm$^2$·s for 3 hours yielded 300 μCi of $^{166}$Ho in 1 mg of $^{166}$Ho-MCM-41 nanoparticles.

A 2470 Wizard Automatic Gamma Counter (PerkinElmer Inc., Waltham, Mass.) was calibrated using a traceable point source (National Institute of Standards and Technology (NIST), U.S. Department of Commerce, Gaithersburg, Md.) and used to measure the $^{166}$Ho content of the $^{166}$Ho-MCM-41 nanoparticles by quantifying the 81 keV photons emitted by $^{166}$Ho. The $^{166}$Ho content of the $^{166}$Ho-MCM-41 nanoparticles was about 20% w/w. For example, in one set of experiments, the $^{166}$Ho content of the $^{166}$Ho-MCM-41 nanoparticles was 20.8±1.9% w/w.

Example 15

$^{166}$Ho-MCM-41 Nanoparticles May be Administered Via Intravenous Injection

Non-tumor athymic mice were intravenously injected with 1 mg $^{166}$Ho-MCM-41 (Example 14; approximately 260 μCi) nanoparticles in 10% PEG 1500 in PBS.

Figure 14:
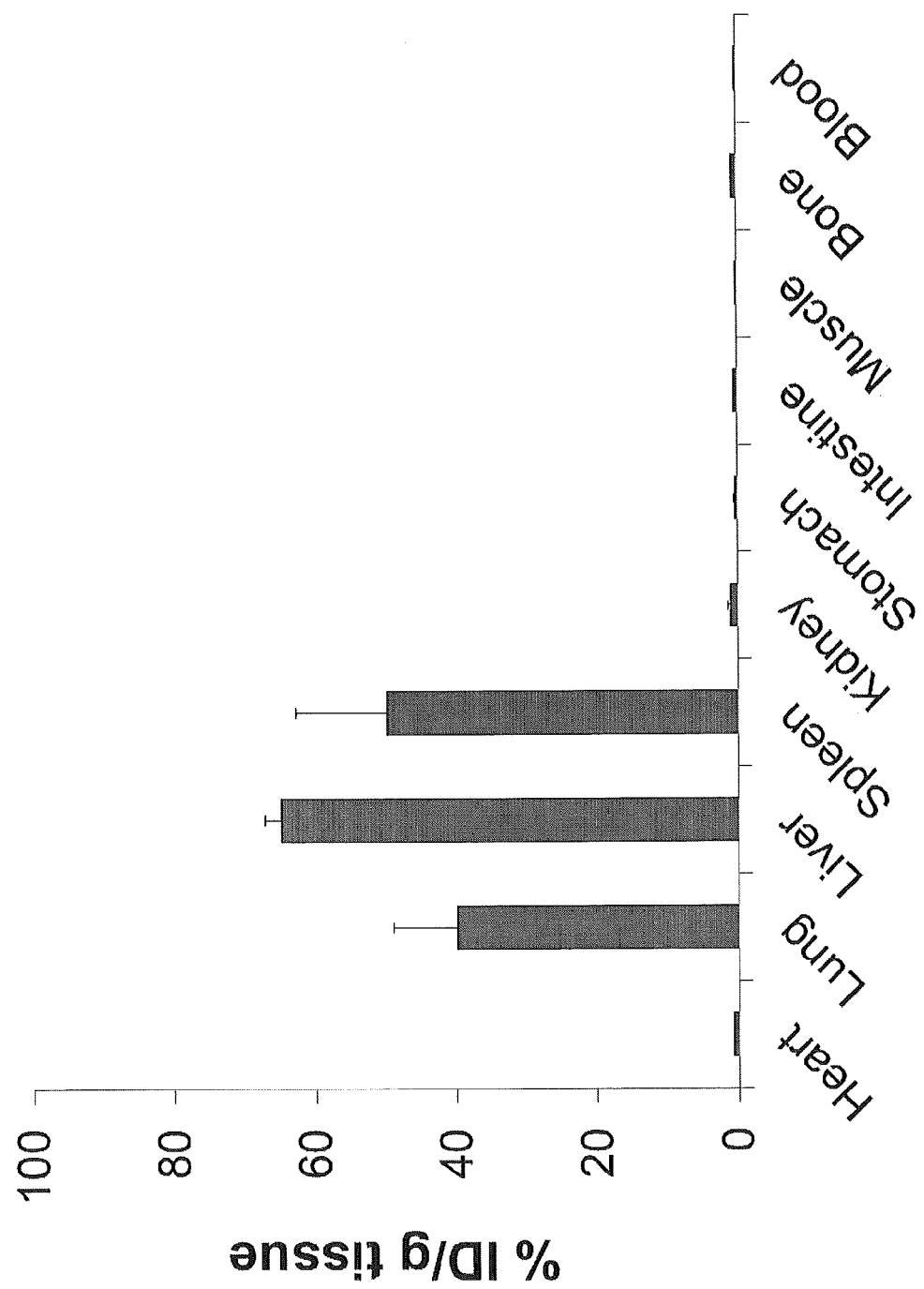
FIG. 14 is a graph that shows the biodistribution of $^{166}$Ho-MCM-41 nanoparticles 24 hours after intravenous injection in athymic (nu/nu) mice.

Biodistribution studies were performed 24 hours after injection. FIG. 14. $^{166}$Ho-MCM-41 nanoparticles were found to have accumulated in the lung, liver and spleen of the mice.

Example 16

$^{166}$Ho-MCM-41 Nanoparticles Accumulate in Tumors

Figure 15A:
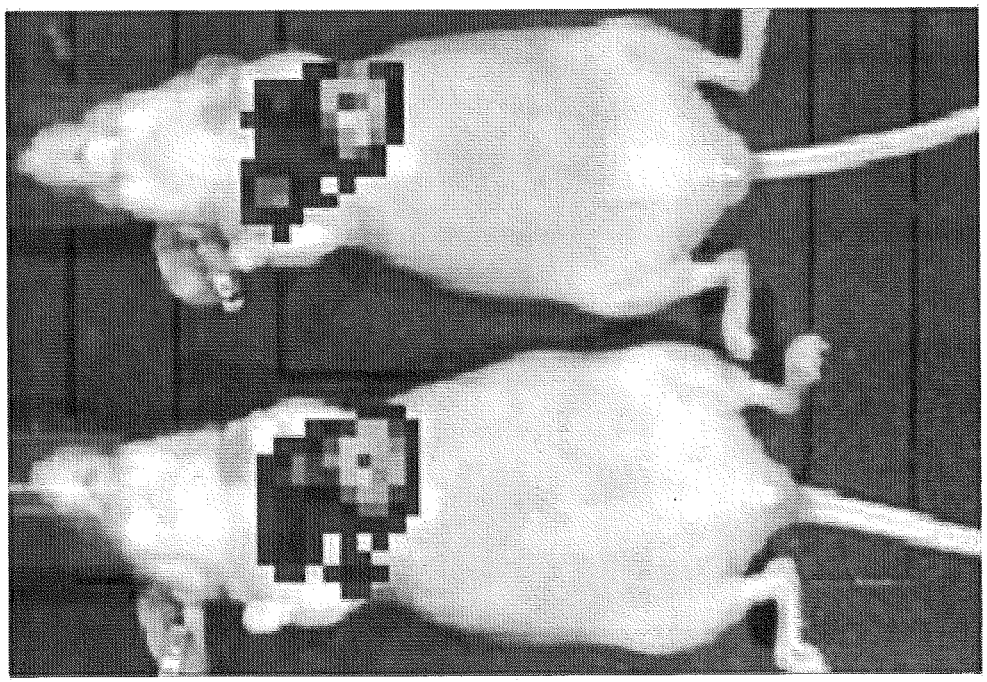
FIGS. 15A, 15B show that intravenously injected $^{166}$Ho-MCM-41 nanoparticles accumulated in the tumors of mice injected with NSCLC A549-luc-C8 cells.

NSCLC A549-luciferase tumor-bearing mice were prepared by injecting approximately one million NSCLC A549-luc-c8 cells into the lung parenchyma of athymic (nu/nu) mice. Implantation and tumor progression were monitored by detecting luciferase bioluminescence following luciferin injections. FIG. 15A.

Fifty to sixty days after implantation, NSCLC A549-luciferase tumor-bearing mice were intravenously injected with $^{166}$Ho(AcAc)$_3$ (approximately 150 μCi), $^{166}$Ho-MCM-41 nanoparticles (Example 14; approximately 150 μCi), $^{166}$Ho(AcAc)$_3$ (approximately 300 μCi) or $^{166}$Ho-MCM-41 nanoparticles (Example 14; approximately 300 μCi) in 100 μL of 10% PEG-1500 in PBS, pH 7.4 (n=4 mice per treatment group).

Figure 15B:
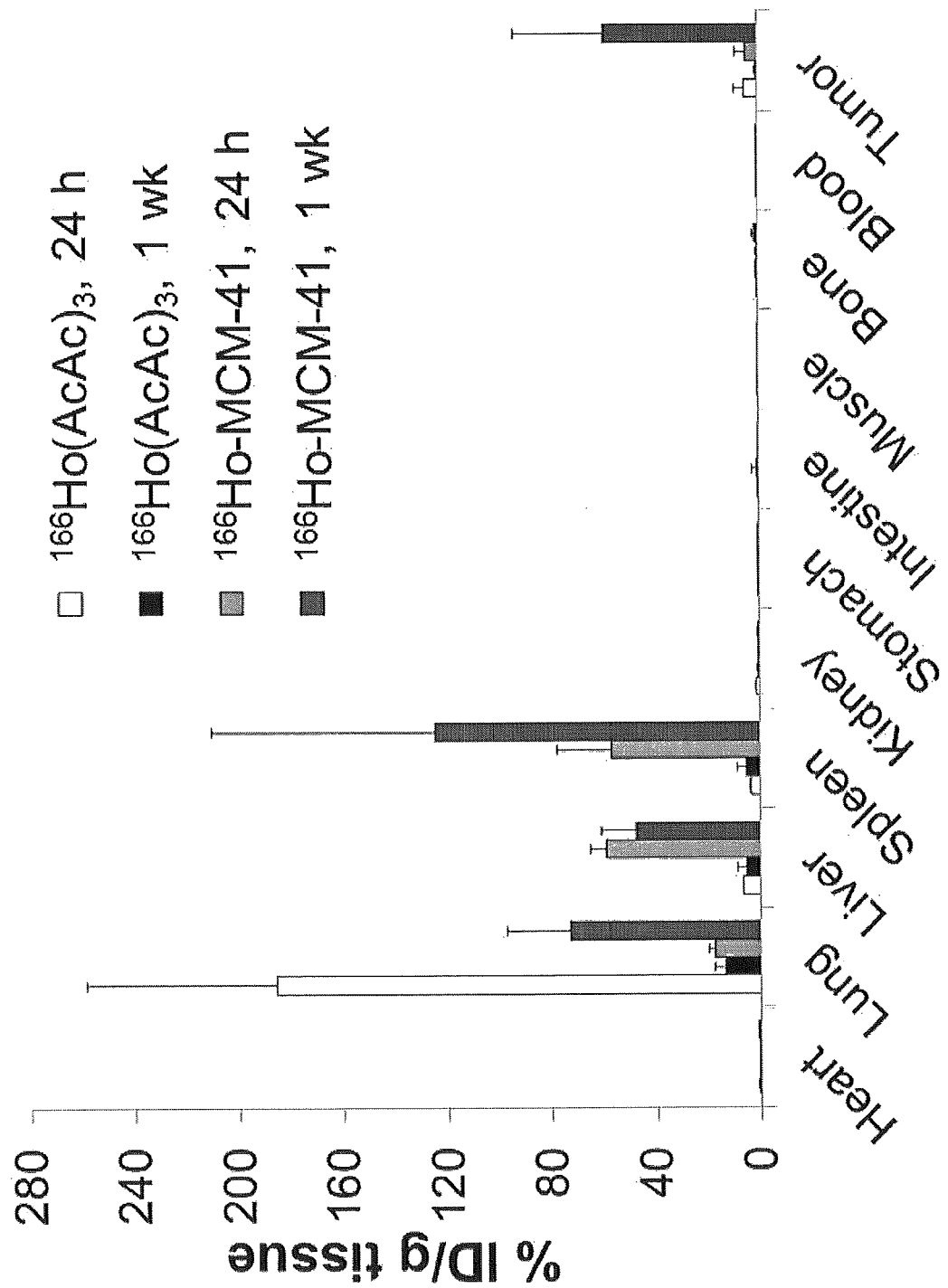

Biodistribution studies were performed 24 hours after i.v. injection with approximately 150 μCi of $^{166}$Ho(AcAc)$_3$ or $^{166}$Ho-MCM-41 nanoparticles or one week after i.v. injection with approximately 300 μCi of $^{166}$Ho(AcAc)$_3$ or $^{166}$Ho-MCM-41 nanoparticles by removing and weighing various organs and quantifying the $^{166}$Ho content of each organ using a 2470 Wizard Automatic Gamma Counter (PerkinElmer Inc., Waltham, Mass.). FIG. 15B. After 24 hours, 4.5±3.9 percent initial dose per gram (% ID/g) was measured in tumors of mice injected with 150 μCi of $^{166}$Ho-MCM-41 nanoparticles. After one week, 58.8±34.7 percent initial dose per gram (% ID/g) was measured in tumors of mice injected with 300 μCi of $^{166}$Ho-MCM-41 nanoparticles. $^{166}$Ho is not retained in the tumors of mice one week after injection with $^{166}$Ho(AcAc)$_3$.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

That which is claimed:

1. A stable activatable particle comprising an activatable radionuclide precursor and a carrier moiety, wherein said activatable radionuclide precursor comprises
   a radionuclide selected from the group consisting of $^{23}$Na, $^{31}$P, $^{56}$Fe, $^{74}$Se, $^{85}$Rb, $^{88}$Sr, $^{89}$Y, $^{127}$I, $^{139}$La, $^{141}$Pr, $^{149}$Sm, $^{150}$Sm, $^{152}$Sm, $^{164}$Dy, $^{165}$Ho, $^{168}$Er, $^{175}$Lu, $^{185}$Re, $^{187}$Re, $^{197}$Au, $^{203}$Tl, and any combination thereof,
   conjugated to a hydrophobic and/or lipophilic moiety selected from the group consisting of acetylacetone, ethyl acetoacetate, 3-methyl-2,4-pentanedione, 3-ethyl-2,4-pentanedione, 2,4-hexanedione, and diethyl malonate, and wherein said carrier moiety is a silica particle having a diameter of about 1 nm to about 500 nm.

2. The stable activatable particle of claim 1, wherein said activatable radionuclide precursor comprises a radionuclide selected from the group consisting of $^{31}$P, $^{88}$Sr, $^{89}$Y, $^{127}$I, $^{149}$Sm, $^{150}$Sm, $^{152}$Sm, $^{164}$Dy, $^{165}$Ho, $^{175}$Lu, and any combination thereof.

3. The stable activatable particle of claim 1, wherein said activatable radionuclide precursor comprises $^{165}$Ho.

4. The stable activatable particle of claim 1, wherein said activatable radionuclide precursor is holmium-165 acetylacetonate ($^{165}$Ho(AcAc)$_3$).

5. The stable activatable particle of claim 1, wherein said carrier moiety is a mesoporous silica particle.

6. The stable activatable particle of claim 1, wherein said carrier moiety comprises a targeting agent.

7. The stable activatable particle of claim 6, wherein said targeting agent is a tumor-targeting agent.

8. A radiotherapeutic agent produced by activating the stable activatable particle of claim 1.

9. The radiotherapeutic agent of claim 8, wherein activating the stable activatable particle comprises neutron activation.

10. A pharmaceutical composition comprising the stable activatable particle of claim 1.

11. A pharmaceutical composition comprising the radiotherapeutic agent of claim 8.

* * * * *